US012653544B2

(12) United States Patent
Shindo et al.

(10) Patent No.: US 12,653,544 B2
(45) Date of Patent: Jun. 16, 2026

(54) CLIP, SYSTEM, AND CLIP DEPLOYMENT METHOD

(71) Applicant: OLYMPUS MEDICAL SYSTEMS CORP., Tokyo (JP)

(72) Inventors: Shogo Shindo, Koganei (JP); Motoi Satake, Kokubunji (JP); Masaru Yuasa, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 363 days.

(21) Appl. No.: 18/172,684

(22) Filed: Feb. 22, 2023

(65) Prior Publication Data

US 2023/0263533 A1 Aug. 24, 2023

Related U.S. Application Data

(60) Provisional application No. 63/362,821, filed on Apr. 11, 2022, provisional application No. 63/268,449, filed on Feb. 24, 2022.

(51) Int. Cl.
*A61B 17/122* (2006.01)
*A61B 17/12* (2006.01)

(52) U.S. Cl.
CPC .... *A61B 17/1227* (2013.01); *A61B 17/12013* (2013.01)

(58) Field of Classification Search
CPC ................ A61B 17/083; A61B 17/122; A61B 17/128–1285; A61B 17/2496; A61B 17/1227; A61B 17/29–295
See application file for complete search history.

(56) References Cited

U.S. PATENT DOCUMENTS

| | | | | |
|---|---|---|---|---|
| 5,976,161 | A * | 11/1999 | Kirsch ................... | A61B 17/11 606/205 |
| 8,695,464 | B2 * | 4/2014 | Herrmann ................ | B25B 7/10 81/413 |
| 10,441,284 | B2 | 10/2019 | Gordon et al. | |
| 12,121,254 | B2 | 10/2024 | Tang et al. | |
| 2015/0057704 | A1 * | 2/2015 | Takahashi ......... | A61B 17/0057 606/221 |

(Continued)

FOREIGN PATENT DOCUMENTS

| | | |
|---|---|---|
| CN | 111481304 A | 8/2020 |
| JP | 2019154978 A | 9/2019 |
| WO | WO-2016040760 A1 | 3/2016 |

*Primary Examiner* — Katherine M Shi
*Assistant Examiner* — Serenity A Miller
(74) *Attorney, Agent, or Firm* — Schwegman Lundberg & Woessner, P.A.

(57) ABSTRACT

A multi-arm clip comprising: a central arm; a pair of outer arms configured to rotatably connect to the central arm; a slide pin configured to move along a longitudinal axis direction of the central arm to open or close the pair of outer arms using an outer arm slot defined by the pair of outer arms; a retention feature provided on either the central arm or each one of the pair of the outer arms, the retention feature configured to maintain a gripping force between the central arm and the pair of outer arms in an adjustable manner; and a force transmitter configured to move the slide pin along the longitudinal axis direction; wherein the pair of outer arms includes an outer arm slot, the outer arm slot configured to make the slide pin movable.

19 Claims, 21 Drawing Sheets

(56) References Cited

U.S. PATENT DOCUMENTS

| | | | |
|---|---|---|---|
| 2016/0228108 A1* | 8/2016 | Raybin | A61B 17/0057 |
| 2020/0353599 A1* | 11/2020 | Gibic | B25B 13/22 |
| 2021/0259700 A1* | 8/2021 | Zhang | A61B 17/1222 |
| 2022/0054156 A1* | 2/2022 | Tang | A61B 17/1285 |
| 2023/0057353 A1* | 2/2023 | Zhang | A61B 17/29 |
| 2023/0059424 A1* | 2/2023 | Barenboym | A61B 17/1285 |

\* cited by examiner

CLIP, SYSTEM, AND CLIP DEPLOYMENT METHOD

CROSS-REFERENCE TO RELATED APPLICATIONS

This application is based upon and claims the benefit of priority to U.S. Provisional Application Ser. No. 63/268,449, filed on Feb. 24, 2022, and U.S. Provisional Application Ser. No. 63/362,821, filed on Apr. 11, 2022, the entire contents of which is incorporated herein by reference.

TECHNICAL FIELD

The present disclosure relates to a clip. More specifically, the present disclosure relates to a multi-arm clip and a tissue closure method using the multi-arm clip.

BACKGROUND

An endoscopy procedure can include use of a clip for ligating a resected tissue portion, such as to facilitate a hemostasis procedures. Generally, the clip is locked in place with excised or cut tissue located therebetween and the clip is deployed within a body lumen.

In the approach of Patent Document 1, Chinese Patent Application Publication No. 111481304, a clip includes a central arm and two outer arms, and the operator can ligate a resected portion of tissue by independently operating the two outer arms.

SUMMARY

In the approach of Patent Document 1, when a tissue such as the resected portion after the treatment that is clamped by the clip is manipulated, such tissue may detach from an arm of the clip. The gripping force by the arm may be increased by the operator, to securely maintain the tissue within the clip; however, it is possible that the tissue may be torn or damaged and such gripping force is not regulated without ongoing input from the operator.

The present disclosure can address such challenges. For example, the present disclosure can include or use a clip and a tissue closure method using the clip capable of gripping tissue with an appropriate gripping force including maintaining a state in which tissue is gripped without requiring an operator to maintain force on an external control, and a related method described herein includes closing tissue using the clip.

According to an aspect of the present disclosure, as an illustration, a three-arm clip includes a central arm; a pair of outer arms configured to rotatably connect to the central arm; a slide pin configured to advance and retract along a longitudinal direction of the central arm; a retention feature provided in either of the central arm and the pair of outer arms and configured to maintain (e.g., in an adjustable manner) a gripping force established between the central arm and the pair of outer arms; a release feature detachably connected to the slide pin; and a force transmitter configured to advance and retract the slide pin that is connected to the release feature, wherein the pair of outer arms includes an outer arm slot in which the slide pin is slidable, and the pair of outer arms actuate when the slide pin advances and retracts along the longitudinal direction to slide in the outer arm slot.

According to another aspect of the present disclosure, a clip includes a central arm including a first pin, a first slot, and a second pin being movable in the first slot; a pair of outer arms including a second slot in which the second pin is slidable, the pair of outer arms being rotatably connected to the central arm by the first pin; a wire detachably connected to the central arm or the pair of outer arms and configured to drive opening and closing operations of the pair of outer arms; and a retention feature including an end provided in the central arm or the pair of outer arms and configured to maintain a gripping force for gripping tissues, such as in an adjustable manner.

According to a further aspect of the present disclosure, a clip deployment method includes gripping a first portion of tissue by a first arm and a central arm; adjusting a gripping force for gripping the first portion to maintain a state in which the first portion is gripped without requiring further force input by an operator; moving the first portion in a direction approaching a second portion of the tissue in the state in which the first portion is gripped by maintaining the gripping force; and gripping the second portion by the central arm and a second arm after the first portion is moved in the vicinity of the second portion.

According to another aspect of the present disclosure, the retention feature includes respective teeth configured to restrict the slide pin from sliding along the outer arm slot.

DETAILED DESCRIPTION

A clip device according to a first example of the present disclosure will be described with reference to FIG. 1 through FIG. 9. A treatment with respect to a biological tissue (defect) as a treatment target using the clip device according to the present disclosure will be described with reference to FIG. 10 through FIG. 13. A clip device according to a first modified example of the present disclosure will be described with reference to FIG. 14 through FIG. 16. A clip device according to a second modified example of the present disclosure will be described with reference to FIG. 17 through FIG. 19.

In the examples described herein, the same reference signs are used for similar components. Further, in the following description, for example, the expressions indicating the relative or absolute arrangement such as "parallel", "orthogonal", "central", and "coaxial" are used to not only describe such arrangements literally, but such terms are also used to describe a state in terms of relative arrangement or separation such that the same function may be obtained even if structures are not strictly parallel, orthogonal, central, or coaxial, for example. The term "patient" as used in the present description includes any living beings and also includes the term "subject". The patient may be a human or an animal.

Figure 1:
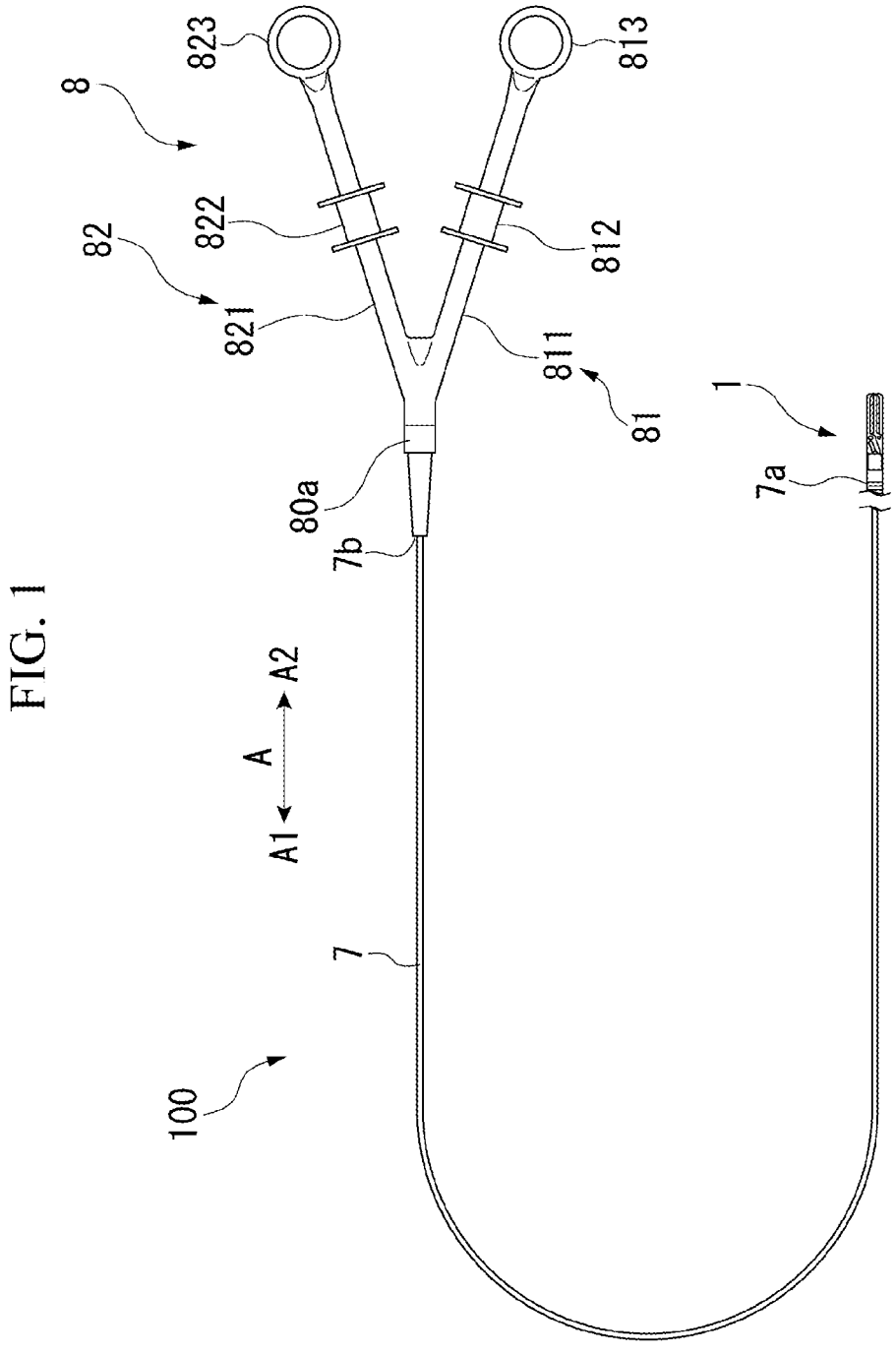
FIG. 1 is a view showing an example of an overall configuration of an endoscopic treatment device (e.g., a system) including a clip according to a first example of the present disclosure.

FIG. 1 is a view showing an overall configuration of the clip device 100. The clip device 100 includes a treatment portion (clip) 1, a pulling member 5 (see FIG. 9), an operation wire 6 (see FIG. 9), a sheath 7, and an operation portion (handle) 8. In the following description, a treatment portion 1 side in the longitudinal direction A of the clip device 100 is defined as a distal end side (distal side) A1 of the clip device 100, and an operation portion 8 side of the clip device 100 is defined as a proximal end side (proximal side) A2 of the clip device 100. In the clip device 100, the treatment portion 1, the pulling member 5, the operation wire 6, the sheath 7, and the operation portion 8 are arranged in this order from the distal end side A1 to the proximal end side A2 of the clip device 100.

The clip device 100 is used with, for example, an endoscope that is not shown in figures. More specifically, the clip device 100 may be used to perform treatment with respect to the biological tissue by an operator operating the operation portion 8 to insert the sheath 7 and the treatment portion 1 provided at the distal end side A1 of the sheath 7 into a treatment device channel formed in the endoscope and introduce the treatment portion 1 to the vicinity of the biological tissue in a lumen as a treatment target. In the present example, the endoscope used together with the clip device 100 may be a flexible endoscope.

Figure 2:
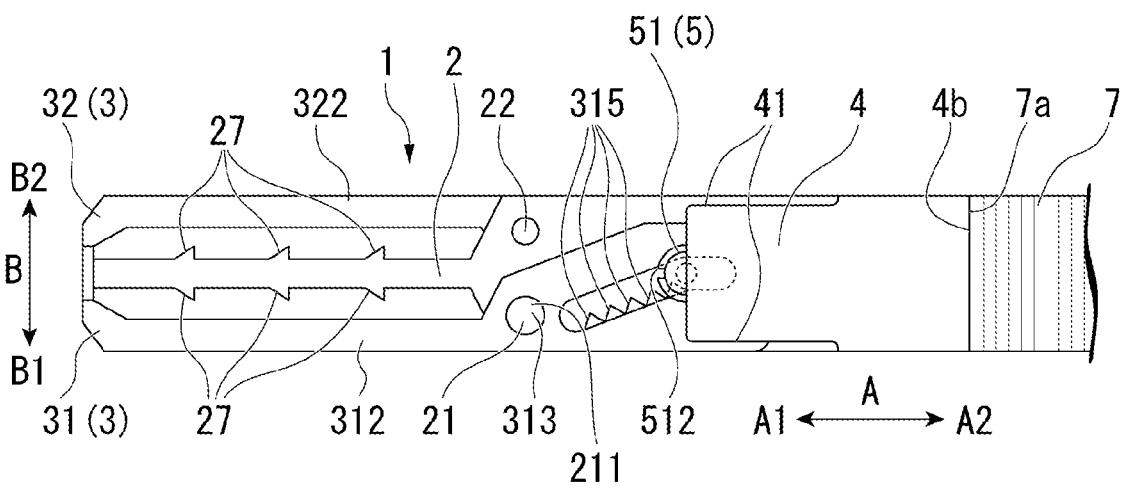
FIG. 2 is a view showing an example of a state in which a treatment portion of the clip is closed.

FIG. 2 is a view showing a state in which the treatment portion 1 of the clip device 100 according to the present example is closed.

The treatment portion (clip) 1 is a clip useful for the therapeutic treatment of a patient such as, for example, prevention of bleeding of tissue, closure of perforation and hemostasis, suture shrink of internal wounds, marking of lesions and tractions (mucosal bumps), and other surgical procedures. The treatment portion 1, as shown in FIG. 2, includes a central arm 2, a pair of outer arms 3, and a clip holder 4. The pair of outer arms 3 includes a first outer arm 31 and a second outer arm 32 configured to open and close with respect to the central arm 2. The first outer arm (first arm) 31 and the second outer arm (second arm) 32 are provided on both sides of the central arm 2 to sandwich the central arm 2 therebetween, and open independently in the opposite direction. That is, the treatment portion 1 of the clip device 100 according to the present example is a three-arm clip including the first outer arm 31, the second outer arm 32, and the central arm 2.

A direction in which the pair of outer arms 3 of the treatment portion 1 opens and closes with respect to the central arm 2 is defined to as an open-close direction B, and a direction in which the first outer arm 31 is opened to be separated from the central arm 2 is referred to as a first side B1. Further, a direction in which the second outer arm 32 is opened to be separated from the central arm 2 is defined to as a second side B2. A direction orthogonal to the longitudinal direction A and the open-close direction B is referred to as a thickness direction C.

[Outer Arm 3]

Figure 3:
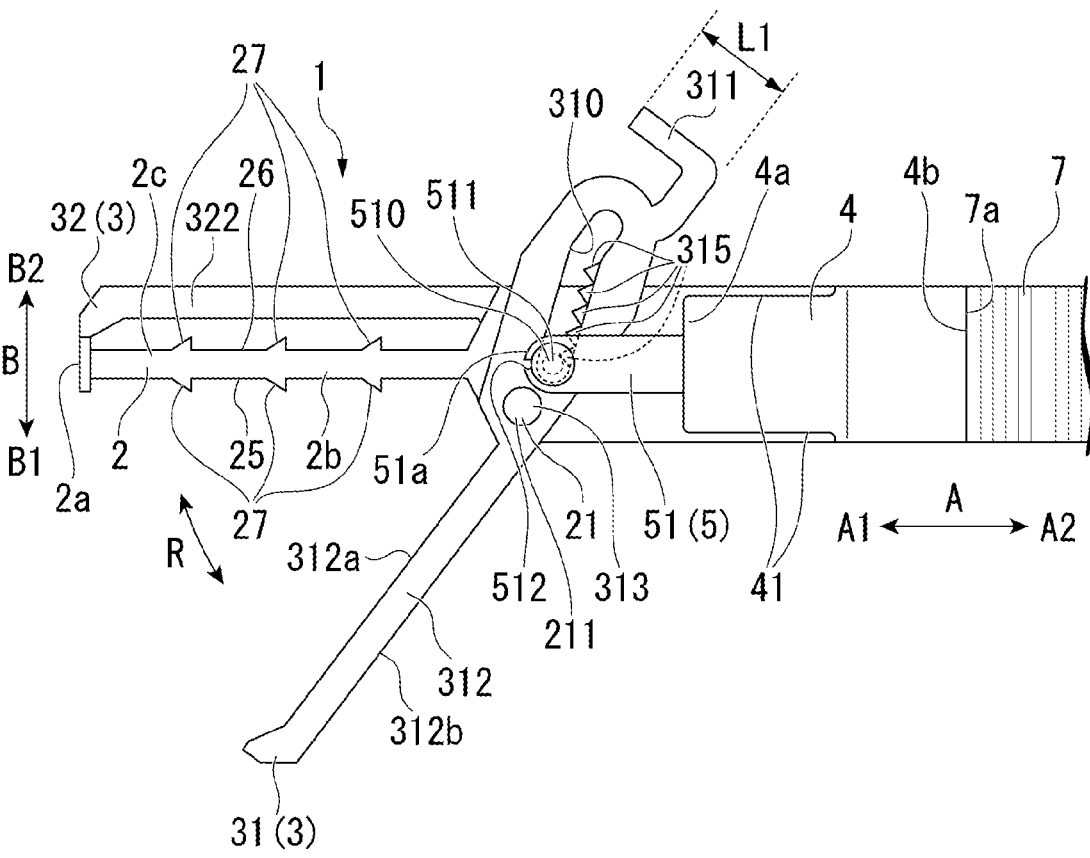
FIG. 3 is a view showing an example of a state in which a first outer arm of the treatment portion of the clip is open.
Figure 4:
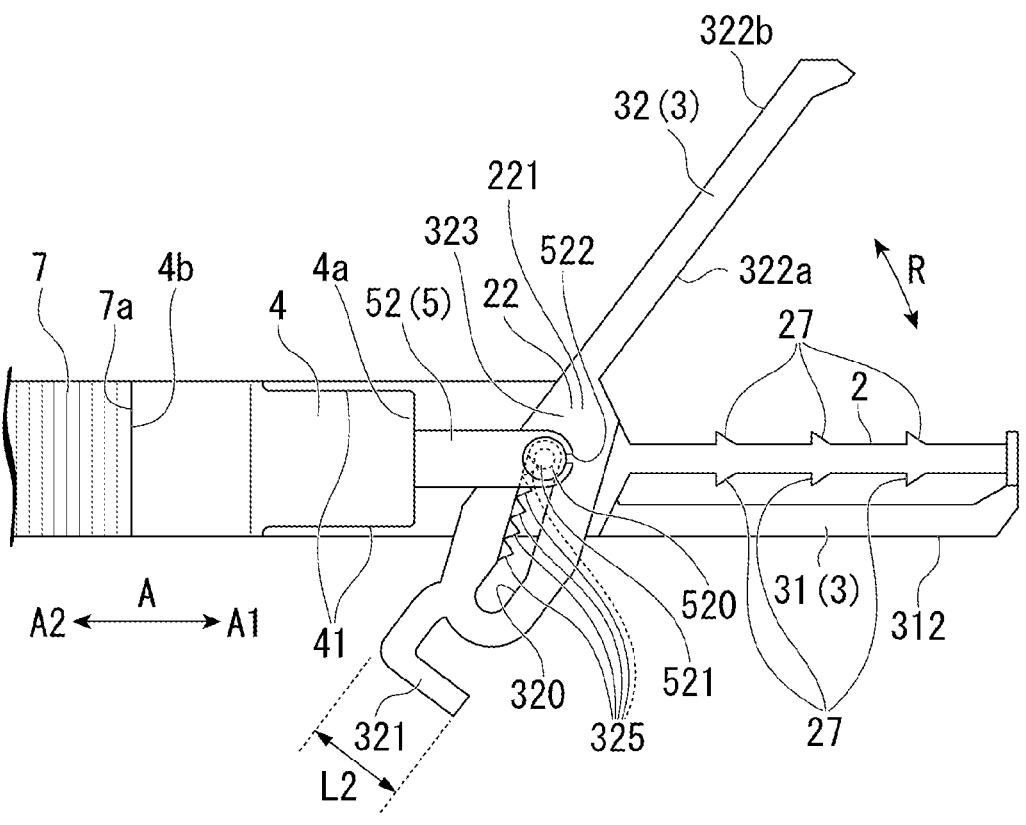
FIG. 4 is a view showing an example of a state in which a second outer arm of the treatment portion of the clip is open.
Figure 5:
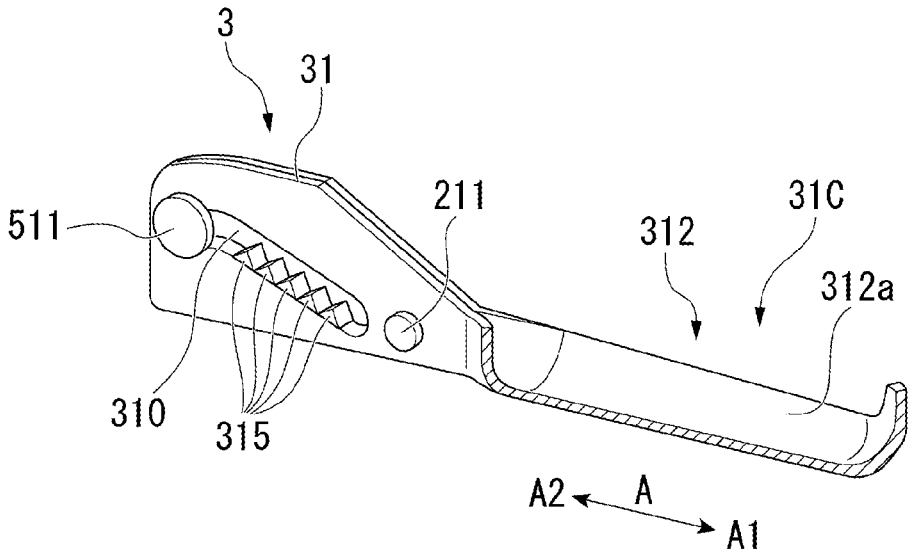
FIG. 5 is a perspective cross-sectional view showing an example of the first outer arm of the treatment portion of the clip according to the present disclosure.
Figure 6:
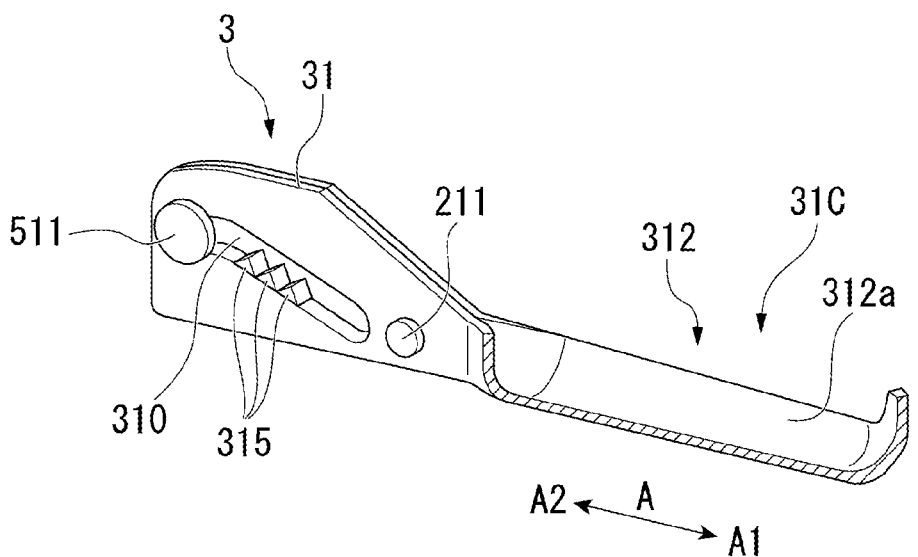
FIG. 6 is a perspective cross-sectional view showing an example of another aspect of the first outer arm of the treatment portion of the clip.

The pair of outer arms 3, as shown in FIG. 2 through FIG. 5, include the first outer arm 31 and the second outer arm 32. FIG. 3 is a view showing a state in which the first outer arm 31 of the treatment portion 1 of the clip device 100 is opened. FIG. 4 is a view showing a state in which the second outer arm 32 of the treatment portion 1 of the clip device 100 is opened. FIG. 5 is a view showing the first outer arm 31 of the treatment portion 1 of the clip device 100 according to the present example. FIG. 6 is a view showing another aspect of the first outer arm 31 of the treatment portion 1 of the clip device 100 according to the present example. The first outer arm 31 is disposed on the first side B1 of the central arm 2 in the open-close direction B. The second outer arm 32 is disposed on the second side B2 of the central arm 2 in the open-close direction B. The first outer arm 31 and the second outer arm 32 can be opened and closed independently.

The first outer arm 31, as shown in FIG. 2 and FIG. 3, is provided in the open-close direction B with respect to the central arm 2 to be openable and closeable. Specifically, the first outer arm 31 is rotatably attached to the central arm 2 by a first rotation pin 211 provided in a first through hole 313. The first outer arm 31 includes a first slide slot 310, a first engaging portion 311, a first through hole 313, and a first arm portion 312.

The first slide slot 310, as shown in FIG. 3, is provided on the proximal end side A2 of the first outer arm 31. The first slide slot 310 engages a first slide pin 511, which will be described later. As shown in FIG. 2 and FIG. 3, on an inner wall of the first slide slot 310 according to the present example, a retention feature comprising a ratchet feature is formed by arranging a plurality of teeth 315 along the longitudinal direction. The plurality of teeth 315 are arranged such as to control the first slide pin 511 of the first pulling member 51, which will be described later, to be advanceable and retractable along the first slide slot 310. More specifically, the advancement and retraction of the first slide pin 511 is restricted by the engagement of the first slide pin 511 with the plurality of teeth 315 and can be used to maintain a gripping force.

As shown in FIG. 5 and FIG. 6, a configuration of the plurality of teeth 315 formed on the inner wall of the first slide slot 310 is shown with respect to the first outer arm 31 according to the present example. As shown in FIG. 5, for example, a plurality of teeth 315 are distributed over the entire longitudinal length of the first slide slot 310 of the first outer arm 31. The plurality of teeth 315 may be formed continuously in the longitudinal direction of the first slide slot 310 or may be formed at predetermined intervals. The plurality of teeth 315 may be formed in the same shape as the same size. The plurality of teeth 315 may have a size such that, for example, when the operator operates the first pulling member 51 to move the first slide pin 511 forward or backward, the first slide pin 511 can ride over the teeth 315. However, when an external force such as an operation by an operator is absent, the first slide pin 511 can be immobilized by teeth 315.

More specifically, in the present example, for example, when the first slide pin 511 rides over any one of the plurality of teeth 315, the slide pin 511 is in a state of being located between the two adjacent teeth 315. In this state, the first slide pin 511 is inhibited from riding over the tooth 315 unless an external force is applied by the operator. As a result, the first slide pin 511 is in a state in which the advancement and retraction of the first slide pin 511 is restricted by the tooth 315. In this state, the relative positional relationship between the first slide pin 511 and the tooth 315 is restricted such that the state in which the first outer arm 31 opens or closes with respect to the central arm 2 is maintained. In other words, since a distance between the first outer arm 31 and the central arm 2 is constrained, if the tissue is located between the first outer arm 31 and the central arm 2, a gripping force with respect to the tissue by the first outer arm 31 and the central arm 2 is maintained without requiring force input by the operator.

As shown in FIG. 6, for example, a plurality of teeth 315 may be distributed within the first slide slot 310 of the first outer arm 31 over about half of the length in the longitudinal length. In particular, the plurality of teeth 315 may be only distributed at the proximal end side along the longitudinal direction. According to such a configuration, the first slide pin 511 may freely advance and retract in the first slide slot 310 until contacting the plurality of teeth 315. As the first slide pin 511 advances and retracts in the first slide slot 310, it is possible to adjust the open-close state of the first outer arm 31 and the central arm 2. Accordingly, the state in which the tissue as the treatment target is gripped by the first outer arm 31 and the central arm 2 may be adjusted. In this manner, it is possible to realize grip or gripping of the tissue as the treatment target by using the treatment portion 1 of the clip device 100.

The first engaging portion 311 is an elastic member having elasticity in the open-close direction B provided on the proximal end side A2 of the first outer arm 31. The first engaging portion 311 is, for example, a leaf spring. The first engaging portion 311 is accommodated within the clip holder 4 when the first outer arm 31 is closed with respect to the central arm 2. More specifically, as shown in FIG. 3, in a state where the first outer arm 31 is opened with respect to the central arm 2, the first engaging portion 311 is positioned outside the clip holder 4 that is described later. On the other hand, as shown in FIG. 2, in a state in which the first outer arm 31 is closed with respect to the central arm 2, the first engaging portion 311 is accommodated within the clip holder 4. In a state in which the first outer arm 31 is closed with respect to the central arm 2, a length L1 of the first engaging portion 311 in the open-close direction B is substantially equal to or substantially larger than an inner diameter of the clip holder 4.

When the first outer arm 31 is transitioned to the open state from the closed state in the open-close direction B with respect to the central arm 2, the first engaging portion 311 is rotated together with the first outer arm 31 and enters the inside of the clip holder 4 from the most proximal end of the first engaging portion 311. In the process of the first engaging portion 311 enters the inside of the clip holder 4, it may be preferable that each portion of the first engaging portion 311 in contact with the clip holder 4 is formed in a rounded shape or having a chamfered profile so as not to damage the inner peripheral surface of the clip holder 4.

The first through hole 313 is a hole that engages with the first rotation pin 211. The first rotation pin 211 connects the first through hole 313 and the through hole 21 provided in the central arm 2. According to this configuration, the first outer arm 31 is rotatable about the first through hole 313 as a center with respect to the central arm 2.

By rotating the first arm portion 312 with respect to the central arm 2 in the open-close direction B, the distal end portion thereof approaches the distal end portion 2a of the central arm 2 such as to grip the tissue. The first arm portion 312 is provided on the distal end side A1 than the first through hole 313 and the first arm portion 312 includes a contact surface 31c formed to be contactable with the tissue. The contact surface 31c includes a first gripping surface (inner surface) 312a and a first outer surface 312b.

The first gripping surface (inner surface) 312a is an inner surface that contacts the tissue in the open-close direction B and faces the central arm 2. The first arm portion 312 is formed by the first gripping surface (inner surface) 312a being recessed toward the first side B1. The first outer surface 312b is a surface provided on a side opposite to the first gripping surface (inner surface) 312a in the open-close direction B. That is, the first arm portion 312 is formed with a recess on the first gripping surface 312a side and a bulge rounded on the first outer surface 312b side in the open-close direction B. Accordingly, when the tissue is gripped by the first outer arm 31 and the central arm 2, the tissue is accommodated in the recessed portion of the first outer arm 31.

The second outer arm 32, as shown in FIG. 2 and FIG. 4, is provided such as to be opened and closed in the open-close direction B with respect to the central arm 2. Specifically, the second outer arm 32 is provided such as to be openable and closable with respect to the central arm 2 in the opposite side of the first outer arm 31 by the second rotation pin 221 provided in the second through hole 323. The second outer arm 32 includes a second slide slot 320, a second engaging portion 321, a second through hole 323, and a second arm portion 322.

In the present example, the second outer arm 32 may have the same configuration as that of the first outer arm 31. That is, on the inner wall of the second slide slot 320 of the second outer arm 32, a ratchet structure is formed by arranging a plurality of teeth 325 along the longitudinal direction. The plurality of teeth 325 are arranged to control the advancement and retraction of the second slide pin 521 of the second pulling member 52, which will be described later, along the second slide slot 320. More specifically, the advancement and retraction of the second slide pin 521 is restricted by the engagement of the second slide pin 521 with the plurality of teeth 325. In the present example, the second outer arm 32 has the same configuration as that of the first outer arm 31 and the duplicate description is omitted.

Figure 7:
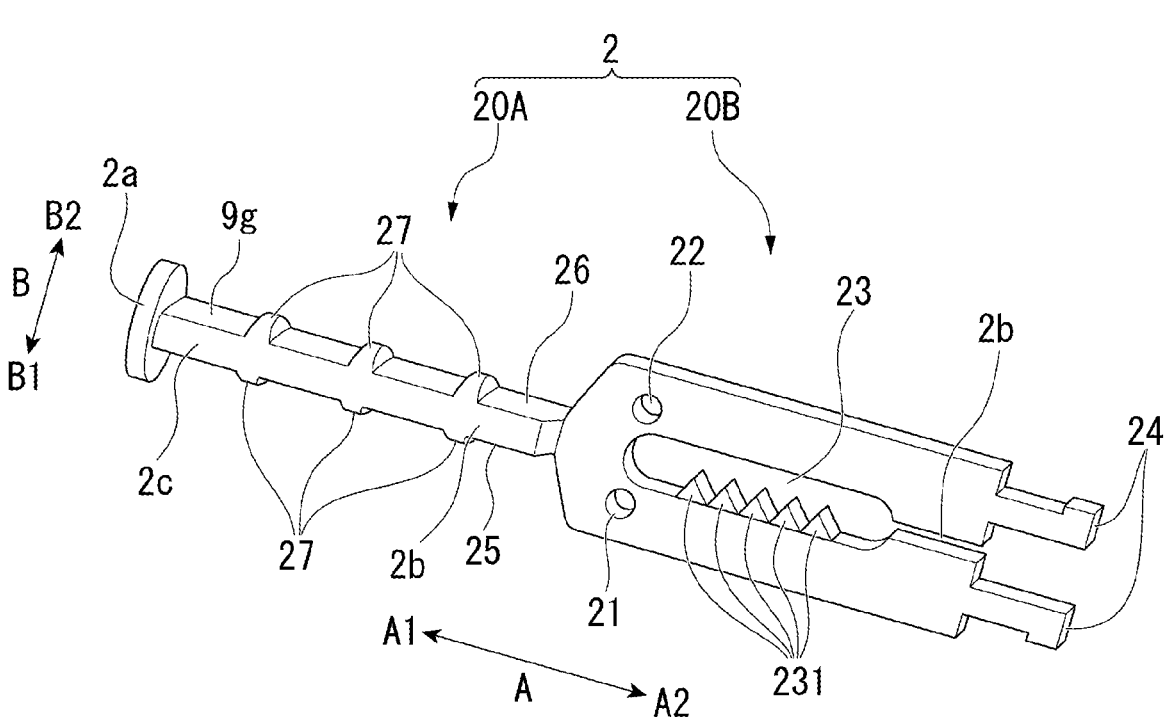
FIG. 7 is a view showing an example of a central arm of the treatment portion of the clip.
Figure 8:
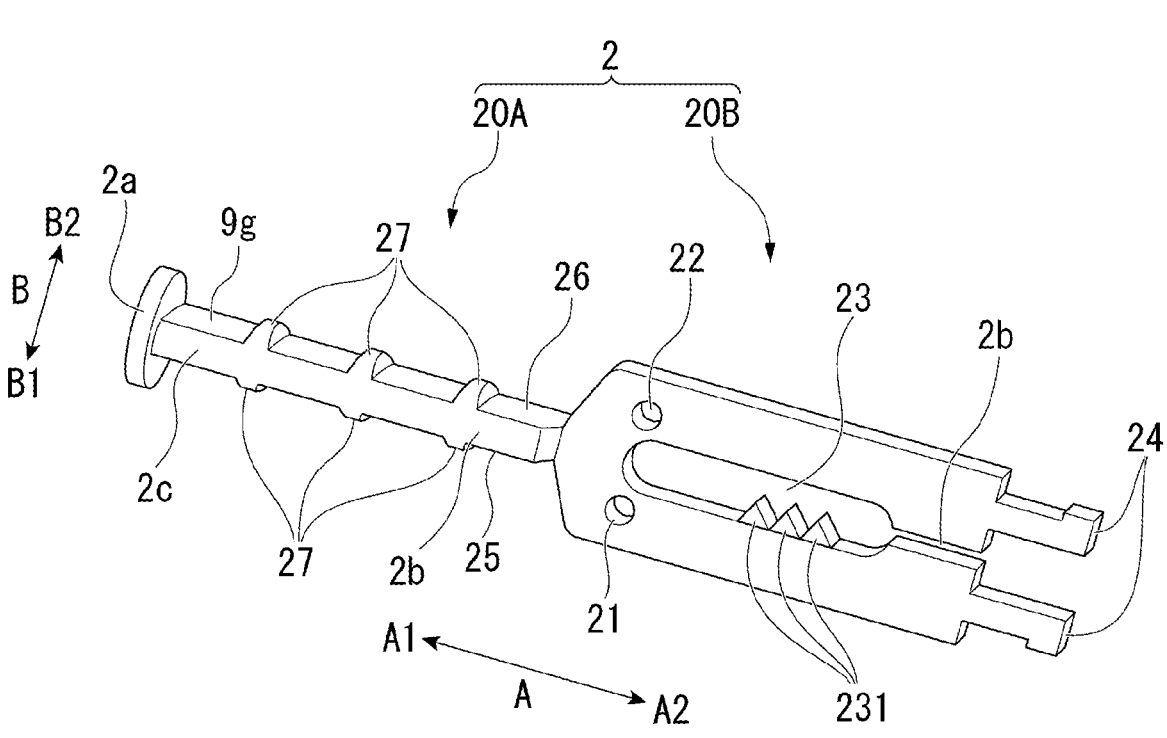
FIG. 8 is a view showing an example of another aspect of the central arm of the treatment portion of the clip.

FIG. 7 is a perspective view showing the central arm 2 of the treatment portion 1 of the clip device 100. FIG. 8 is a side view showing the configuration of the central arm 2 according to the present example. FIG. 9 to FIG. 12 are views showing different configurations of the central arm 2 according to the present example.

As shown in FIG. 2, the central arm 2 is a rod-shaped member provided between the pair of outer arms 3 along the longitudinal direction A. The central arm 2 includes a rod portion 20A formed on the distal end side A1, and a connecting portion 20B formed on the proximal end side A2.

The rod portion 20A, for example, as shown in FIG. 7, comprises a substantially round rod-shaped member formed of a material having the biocompatibility. The entire outer surface of the rod portion 20A is exposed and the rod portion 20A has a contact surface 2c that can contact tissue. The rod portion 20A includes a distal end portion 2a and the rod-shaped portion 2b.

The distal end portion 2a is provided at the distal end of the rod-shaped portion 2b. The distal end portion 2a is formed in a substantially disc shape having a diameter dimension larger than the diameter of the rod-shaped portion 2b, as compared with the rod-shaped portion 2b. Accordingly, the central arm 2 may be locked the central arm 2 to the tissue by hooking the distal end portion 2a to the tissue.

The rod-shaped portion 2b is a substantially round rod-shaped member, and the distal end portion 2a is provided at the distal end thereof. The rod-shaped portion 2b includes a first opposite surface (opposite surface) 25 and a second facing surface (opposite surface) 26, and a plurality of protrusions 27 formed on the first facing surface 25 and the second facing surface 26.

The first facing surface (facing surface) 25 is formed in the rod-shaped portion 2b of the contact surface 2c, and the first facing surface 25 is a surface being opposite to the first outer arm 31 provided on the first side B1 in the open-close direction B.

The second facing surface (facing surface) 26 is formed in the rod-shaped portion 2b of the contact surface 2c, and the second facing surface 26 is a surface being opposite to the first outer arm 31 provided on the first side B1 in the open-close direction B.

The connecting portion 20B is provided on the proximal end side A2 of the rod portion 20A. The connecting portion 20B is formed in a plate shape, and a thickness direction of the connection portion 20B substantially coincides with the thickness direction C. The connecting portion 20B is configured to connect the central arm 2 and the pair of outer arms 3, the clip holder 4 to be described later, and the pulling member 5. The connecting portion 20B, as shown in FIG. 7, comprises a through hole 21, a through hole 22, an engaging groove (central arm slot) 23, and a tail 24.

The through hole 21 is a hole penetrating the connecting portion 20B in the thickness direction C. The through hole 21 is formed on the distal end-side A1 of the connecting portion 20B. The through hole 21 is engaged by the first rotation pin 211.

The through hole 22 is a hole penetrating the connecting portion 20B in the thickness direction C. The through hole 22 is formed on the distal end-side A1 of the connecting portion 20B. The through hole 22 is disposed at substantially the same position with that of the through hole 21 in the longitudinal direction A. The through hole 21 is engaged by the first rotation pin 211. The through hole 22 is engaged by the second rotation pin 221.

The engaging groove 23 is a groove formed on the connecting portion 20B to extend along the longitudinal direction A. The engaging groove 23 is configured to engage with the first slide pin 511 such that the first slide pin 511 is advanceable and retractable along the engaging groove 23.

The tail 24 is formed at the proximal end side A2 of the connecting portion 20B of the central arm 2. The tail 24 is connected to the clip holder 4, which will be described later.

As shown in FIG. 8, in the central arm 2 according to the present example, a plurality of protrusions 27 are formed on the first facing surface 25 and the second facing surface 26.

As shown in FIG. 2 and FIG. 7, the plurality of protrusions 27 are protrusions provided on the central arm 2. The plurality of protrusions 27 include a first protrusion 27a provided on the first facing surface 25 and a second protrusion 27b provided on the second facing surface 26. The first protrusion 27a protrudes from the first facing surface 25 toward the first outer arm 31 disposed on the first side B1 of the open-close direction B. The second protrusion 27b protrudes from the second facing surface 26 toward the second outer arm 32 disposed on the second side B2 of the open-close direction B.

In the present example, as shown in FIG. 7, a plurality of teeth 231 are formed in the engaging groove 23 along the longitudinal direction of the central arm 2. As shown in FIG. 7, the plurality of teeth 231 are distributed over the entire length of the engaging groove 23 in the longitudinal direction. The plurality of teeth 231 may be formed continuously in the longitudinal direction of the engaging groove 23 and may be formed at predetermined intervals. The plurality of teeth 231 may be formed in the same shape and the same size. Each of the plurality of teeth 231 may have a size such that, for example, when the operator operates the first pulling member 51 to advance and retract the first slide pin 511, the first slide pin 511 may ride over the plurality of teeth 231. However, when there is no external force applied by the operator, the first slide pin 511 is inhibited from riding over the teeth 231.

More specifically, in the present example, for example, when the first slide pin 511 rides over any one of the plurality of teeth 231, the first slide pin 511 enters a state of being located between the two adjacent teeth 231. In this state, the first slide pin 511 is inhibited from riding over the tooth 231 in the absence of an external force applied by the operator. Accordingly, the advancement and the retraction of the first slide pin 511 is restricted by the teeth 231. In this state, since the relative positional relationship between the first slide pin 511 and the plurality of teeth 231 is restricted, the state in which the first outer arm 31 opens and closes with respect to the central arm 2 is maintained. In other words, since the distance between the first outer arm 31 and the central arm 2 is constant, in the case in which the tissue is located between the first outer arm 31 and the central arm 2, the force for gripping the tissue by the first outer arm 31 and the central arm 2 is maintained within the grip of the first outer arm 31 and the central arm 2.

As shown in FIG. 8, for example, the plurality of teeth 231 may be distributed over about half of the length in the longitudinal direction in the engaging groove 23 of the central arm 2. For example, the plurality of teeth 231 may be distributed only at the proximal end side along the longitudinal direction in the engaging groove 23 of the central arm 2. According to the configuration, it is possible for the first slide pin 511 to freely advance and retract in the engaging groove 23 until the first slide pin 511 contacts the plurality of teeth 231. Accordingly, as the first slide pin 511 advances and retracts in the engaging groove 23, it is possible to adjust the open-close state of the first outer arm 31 and the central arm 2. Therefore, the state in which the tissue as the treatment target is gripped by the first outer arm 31 and the central arm 2 may be adjusted. That is, according to the configuration, it is possible to realize release or the gripping of the tissue as the treatment target by using the treatment portion 1 of the clip device 100 according to the present example.

As described above, the configuration in which the plurality of teeth 315 and 325 are formed in the first slide slot 310 of the first outer arm 31 and the second slide slot 320 of the second outer arm 32 respectively, and the configuration in which the plurality of teeth 231 are formed in the engaging groove 23 of the central arm 2 have been described. However, the clip device 100 according to the present example may include either of the above-described two configurations. For example, a configuration may be made such that the plurality of teeth 315, 325 are formed in the first slide slot 310 of the first outer arm 31 and the second slide slot 320 of the second outer arm 32 while there is no tooth 231 being formed in the engaging groove 23 of the central arm 2. Another configuration may be made such that the plurality of teeth 231 are formed in the engaging groove 23 of the central arm 2 instead of forming the plurality of teeth 315, 325 in each of the first slide slot 310 of the first outer arm 31 and the second slide slot 320 of the second outer arm 32.

[Clip Holder 4]

The clip holder 4, as shown in FIG. 2, has a longitudinal axis, and the clip holder 4 is a tubular structure, such as formed in a cylindrical shape. In the present example, the clip holder 4 is arranged along the longitudinal direction A. The clip holder 4 is configured for at least the proximal end portion of the outer arm 3 and the central arm 2 in the closed state to enter.

The clip holder 4 has a groove portion 41. The groove portion 41 is formed at a distal end side A1 of the clip holder 4 and at the first side B1 and the second side B2 of the open-close direction B. The groove portion 41 is, for example, a slit formed from the distal end toward the proximal end side A2, and the groove portion 41 has the dimension suitable for the first engaging portion 311 of the first outer arm 31 and the second engaging portion 321 of the second outer arm 32 to enter.

In the clip holder 4, for example, an engaging hole to which a pair of tails 24 of the central arm 2 are engaged may be formed on the proximal end. Accordingly, the central arm 2 is attached to the clip holder 4. The central arm 2 and the clip holder 4 may be integrally formed.

The clip holder 4 has an inner diameter being the same or slightly shorter than the length L1 of the first engaging portion 311 and the length L2 of the second engaging portion 321. The clip holder 4 may accommodate the first engaging portion 311 and the second engaging portion 321 therein. When the first outer arm 31 is rotated to the second side B2 in the open-close direction B, the first engaging portion 311 enters the inside of the clip holder 4 from the groove 41. Also, when the second outer arm 32 is rotated to the first side B1 in the open-close direction B, the second engaging portion 321 enters the inside of the clip holder 4 from the groove 41. Until the first engaging portion 311 is engaged with and locked to the clip holder 4, the first outer arm 31 may be opened again with respect to the central arm 2. Also, until the second engaging portion 321 is engaged with and locked to the clip holder 4, the second outer arm 32 may be opened again with respect to the central arm 2.

In a state where the first engaging portion 311 is accommodated in the inside of the clip holder 4, when the first engaging portion 311 is further retracted to the proximal end side A2, the first engaging portion 311 is in contact with the inner peripheral surface of the clip holder 4 and elastically deformed such as to be engaged with and locked to the interior of the clip holder 4. Further, in a state in which the second engaging portion 321 is accommodated in the interior of the clip holder 4, when the second engaging portion 321 is further retracted to the proximal end side A2, the second engaging portion 321 is in contact with the inner peripheral surface of the clip holder 4 and elastically deformed such as to be engaged with and locked to the interior of the clip holder 4. Accordingly, the closed state of the first outer arm 31 and the second outer arm 32 with respect to the central arm 2 is maintained. The clip holder 4 may be configured to lock only one of the first engaging portion 311 and the second engaging portion 321 at first.

Figure 9:
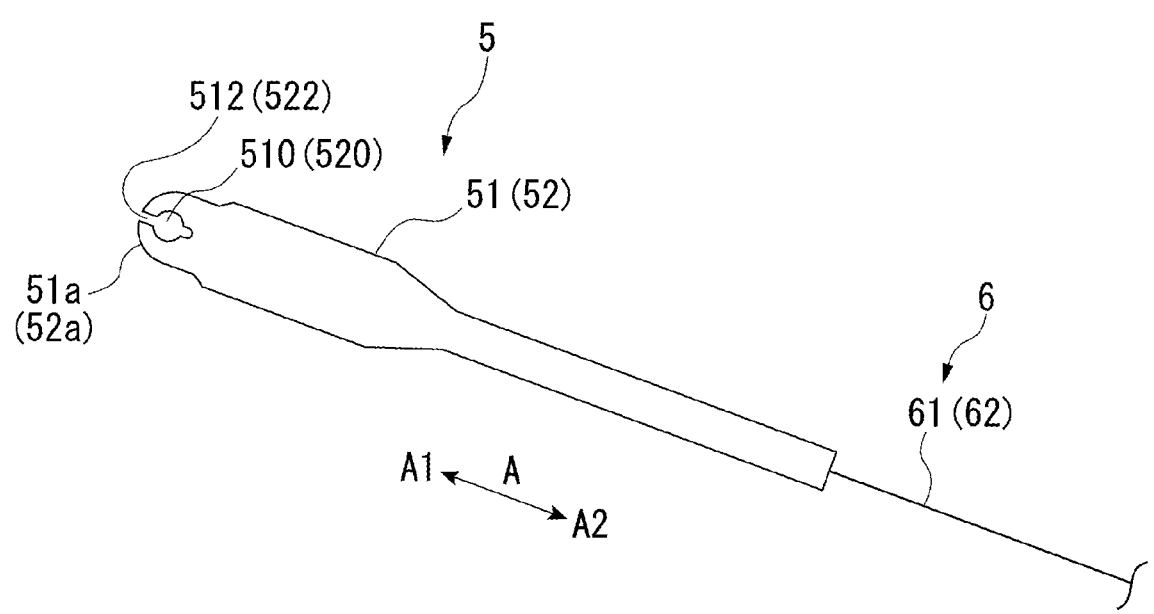
FIG. 9 is a view showing an example of a pulling member and an operation wire of the clip.

FIG. 9 is a view showing the pulling member 5 of the clip device 100.

As shown in FIG. 9, the pulling member 5 includes a first pulling member 51 and a second pulling member 52. The first pulling member 51 and the second pulling member 52 have substantially the same configuration.

The distal end portion 51a of the first pulling member 51 is connected to the proximal end side A2 of the first outer arm 31. Also, the proximal end side A2 of the first pulling member 51 is connected to the distal end portion of the first operation wire 61. The first pulling member 51 includes a first slide pin hole 510 and the first slide pin 511 at the distal end portion thereof.

The first slide pin hole 510 is a hole provided in the distal end portion 51*a* of the first pulling member 51. The first slide pin hole 510 is engageable with the first slide pin 511. The first slide pin hole 510 includes a notch portion 512 on the distal end side A1.

The first slide pin 511 is configured to connect the first slide pin hole 510, the first slide slot 310 of the first outer arm 31, and the engaging groove 23. The first slide pin 511 may advance and retract along the first slide slot 310 and the engaging groove 23 by a sliding operation of a first slider 812 of the operation portion 8 along the longitudinal direction A. When the first slide pin 511 advances toward the distal end side A1 along the first slide slot 310 and the engaging groove 23, the first outer arm 31 is rotated to be opened in the open-close direction B around the first rotation pin 211 as the center to be in the open state with respect to the central arm 2. When the first slide pin 511 retracts toward the proximal end side A2 along the first slide slot 310 and the engaging groove 23, the first outer arm 31 is rotated to be closed in the open-close direction B around the first rotation pin 211 as the center to be in the closed state with respect to the central arm 2. Here, the closed state of the first outer arm 31 with respect to the central arm 2 includes the state in which the distance between the distal end of the first outer arm 31 and the distal end of the central arm 2 is substantially zero. In the state, the first outer arm 31 and the central arm 2 are configured to hold the biological tissues captive as the treatment target between the first outer arm 31 and the central arm 2.

In the present example, when the first slide pin 511 advances and retracts along the first slide slot 310, it is possible for the first slide pin 511 to abut to the plurality of teeth 315 formed on the inner wall of the first slide slot 310 and then ride over the plurality of teeth 315. When the first slide pin 511 abuts to and rides over any one of the plurality of teeth 315, a force applied by the operator who operates the first pulling member 51 becomes larger than in the situation in which the first slide pin 511 advances and retracts in the first slide slot 310 in the absence of the plurality of teeth 315. Accordingly, it is possible for the operator to recognize that the first slide pin 511 engages with and rides over the teeth 315 from the operation feeling at the hand. At this time, even the operator does not continue gripping the operation portion 8 described later at the hand side, the state in which the tissue is gripped by the first outer arm 31 and the central arm 2 is maintained.

The distal end portion 52*a* of the second pulling member 52 is connected to the proximal end side A2 of the second outer arm 32, and the proximal end side A2 of the second pulling member 52 is connected to the distal end portion of the second operation wire 62. The second pulling member 52 has a second slide pin hole 520 and a second slide pin 521 at the distal end portion 52*a*.

The second slide pin hole 520 is a hole provided in the distal end portion 52*a* of the second pulling member 52 and be engageable by the second slide pin 521. The second slide pin hole 520 includes a notch portion 522 on the distal end side A1.

The second slide pin 521 is configured to connect the second slide pin hole 520, the second slide slot 320 of the second outer arm 32, and the engaging groove 23. The second slide pin 521 may advance and retract along the second slide slot 320 and the engaging groove 23 by a sliding operation of a second slider 822 of the operation portion 8 along the longitudinal direction A. When the second slide pin 521 advances toward the distal end side A1 along the second slide slot 320 and the engaging groove 23, the second outer arm 32 is rotated to be opened in the open-close direction B around the second rotation pin 221 as the center to be in the open state with respect to the central arm 2. When the second slide pin 521 retracts toward the proximal end side A2 along the second slide slot 320 and the engaging groove 23, the second outer arm 32 is rotated to be closed in the open-close direction B around the second rotation pin 221 as the center to be in the closed state with respect to the central arm 2. Accordingly, it is possible for the second outer arm 32 to be opened and closed with respect to the central arm 2 in the open-close direction. Here, the closed state of the second outer arm 32 with respect to the central arm 2 includes the state in which the distance between the distal end of the second outer arm 32 and the distal end of the central arm 2 is substantially zero. In the state, the targeted biological tissue is held captive between the second outer arm 32 and the central arm 2.

In the present example, in the case in which the second slide pin 521 advances and retracts along the second slide slot 320, it is possible for the second slide pin 521 to abut to the plurality of teeth 325 formed on the inner wall of the second slide slot 320 and then ride over the plurality of teeth 325. When the second slide pin 521 abuts to and rides over any one of the plurality of teeth 325, a necessary force for the operator who operates the second pulling member 52 becomes larger than in the situation in which the second slide pin 521 advances and retracts in the second slide slot 320 where the plurality of teeth 325 are not formed. Accordingly, it is possible for the operator to recognize that the second slide pin 521 engages with and rides over the teeth 325 from the operation feeling at the hand. At this time, even the operator does not continue gripping the operation portion 8 described later at the hand side, the state in which the tissue is gripped by the second outer arm 32 and the central arm 2 is maintained.

In a state in which the first outer arm 31 is closed with respect to the central arm 2 and the first engaging portion 311 is locked inside the clip holder 4, the first slider 812 of the operation portion 8 is further operated to slide toward the proximal end side A2. Then, the notch portion 512 is deformed or broken, and is detached from the first slide pin 511. The first pulling member 51 is separated from the central arm 2 and the first outer arm 31 which has been connected. In a state in which the second outer arm 32 is closed with respect to the central arm 2 and the second engagement portion 321 is locked to the inside of the clip holder 4, the second slide pin 521 slides toward the proximal end side A2 by operating the second slider 622 of the operation portion 8 toward the proximal end side A2. Then, the notch portion 522 is deformed or broken, and is detached from the second slide pin 521. The second pulling member 52 is separated from the central arm 2 and the second outer arm 32 which has been connected. When the first pulling member 51 and the second pulling member 52 are separated from the central arm 2, the first outer arm 31, and the second outer arm 32, respectively, the treatment portion 1 including the central arm 2, the outer arm 3, and the clip holder 4 in the clip device 100 may be placed in the lumen in the state in which the tissue is gripped.

The operation wire 6 has a first operation wire 61 and a second operation wire 62, as shown in FIG. 9. The first operation wire 61 and the second operation wire 62 have substantially the same configuration.

In the first operation wire 61, a distal end portion thereof is connected to the proximal end portion of the first pulling member 51. A proximal end portion of the first operation wire 61 is fixed to the first slider 812 of the operation portion 8. The first operation wire 61 is inserted into the sheath 7 to be advanceable and retractable. The first operation wire 61 may be formed of, for example, a single wire or a twisted wire made of metal. Regarding the first operation wire 61, the outer peripheral surface may be covered with a non-conductive member or the like. The first operation wire 61 may be fixed to the first pulling member 51 by various methods, for example, adhesive or welding. The first operation wire 61 is configured to advance and retract the first pulling member 51 by the first slider 812 of the operation portion 8 attached to the proximal end portion thereof being operated to slide.

In the second operation wire 62, a distal end portion thereof is connected to the proximal end portion of the second pulling member 52. A proximal end portion of the second operation wire 62 is fixed to the second slider 822 of the operation portion 8. The second operation wire 61 is inserted into the sheath 7 to be advanceable and retractable. The second operation wire 62 may be formed of, for example, a single wire or a twisted wire made of metal. Regarding the second operation wire 62, the outer peripheral surface may be covered with a non-conductive member or the like. The second operation wire 62 may be fixed to the second pulling member 52 by various methods, for example, adhesive or welding. The second operation wire 62 is configured to advance and retract the second pulling member 52 by the second slider 812 of the operation portion 8 attached to the proximal end portion thereof being operated to slide.

The sheath 7 is configured to extend along the longitudinal direction A, for example, as shown in FIG. 1, and is an elongated member insertable into the lumen. The sheath 7 is formed of a material having an insulating property, for example, a fluororesin such as PTFE (polytetrafluoroethylene) or a resin material such as HDPE (high-density polyethylene). The sheath 7 may have the flexibility and the shape of the sheath 7 may be easily changed following the curved shape of the luminal organs inside the lumen, and the sheath 7 is configured such as to be insertable into or withdrawn from a channel (not shown) of the clip device 100. A proximal end portion 7b of the sheath 7 is connected to the operation portion 8, and a distal end portion 7a is connected to the proximal end portion 4b of the clip holder 4. Also, the sheath 7 can receive the first operation wire 61 and the second operation wire 62.

The operation portion (handle) 8 includes a distal end portion 80a, a first operation portion 81, and a second operation portion 82, as shown in FIG. 1. As shown in FIG. 1, the distal end portion 80a is connected to the proximal end portion 7b of the sheath 7. The first operation portion 81 and the second operation portion 82 are connected to the distal end portion 80a and extend in two directions from the distal end portion 80a toward the proximal end side A2.

The first operation portion 81 includes a first operation portion main body 811, a first slider 812, and a finger holding portion 813.

The first operation portion main body 811 is configured to operate the first pulling member 51 and the first outer arm 31 via the first operation wire 61. The first operation portion main body 811 of the first operation portion 81 is formed in a rod shape extending in the longitudinal direction A.

The first slider 812 is configured in the first operation portion main body 811 to be slidable in the longitudinal direction A. The proximal end of the first operation wire 61 is fixed to the first slider 812. The first slider 812 is configured to be inserted through the first operation portion main body 811. When the first slider 812 is advanced and retracted in the longitudinal direction A along the first operation portion main body 811, the first pulling member 51 fixed to the distal end of the first operation wire 61 is advanced and retracted together with the first operation wire 61 along the longitudinal direction A.

The finger holding portion 813 is a substantially ring-shaped portion for holding the fingers and formed on the proximal end side A2 of the first operation portion main body 811.

The second operation portion 82 includes a second operation portion main body 821, a second slider 822, and a finger holding portion 823.

The second operation portion main body 821 is configured to operate the second pulling member 52 and the second outer arm 32 via the second operation wire 62. The second operation portion main body 821 of the second operation portion 82 is formed in a rod shape extending in the longitudinal direction A.

The second slider 822 is configured in the second operation portion main body 821 to be slidable in the longitudinal direction A. The proximal end of the second operation wire 62 is fixed to the second slider 822. The second slider 822 is configured to be inserted through the second operation portion main body 821. When the second slider 822 is advanced and retracted in the longitudinal direction A along the second operation portion main body 821, the second pulling member 52 fixed to the distal end of the second operation wire 62 is advanced and retracted together with the second operation wire 62 along the longitudinal direction A.

The finger holding portion 823 is a substantially ring-shaped portion for holding the fingers and formed on the proximal end side A2 of the second operation portion main body 821.

Next, operations and effects of the clip device 100 will be described with reference to FIG. 10 to FIG. 13. In the present example, as an example of a usage method of the clip device 100, a treatment of ligating a wound (defect) in a body tissue, that is, a tissue closure method will be described. In the present example, in order to simplify the description, the operations of the clip device 100 will be described by taking a configuration in which the plurality of teeth 315, 325 are formed in the first slide slot 310 of the first outer arm 31 and the second slide slot 320 of the second outer arm 32 of the treatment portion 1 respectively as an example; however, the present example is not limited thereto. The configuration in which the plurality of teeth 231 are provided in the engaging groove 23 of the central arm 2 of the treatment portion 1 may also be operated in the same manner.

Figure 10:
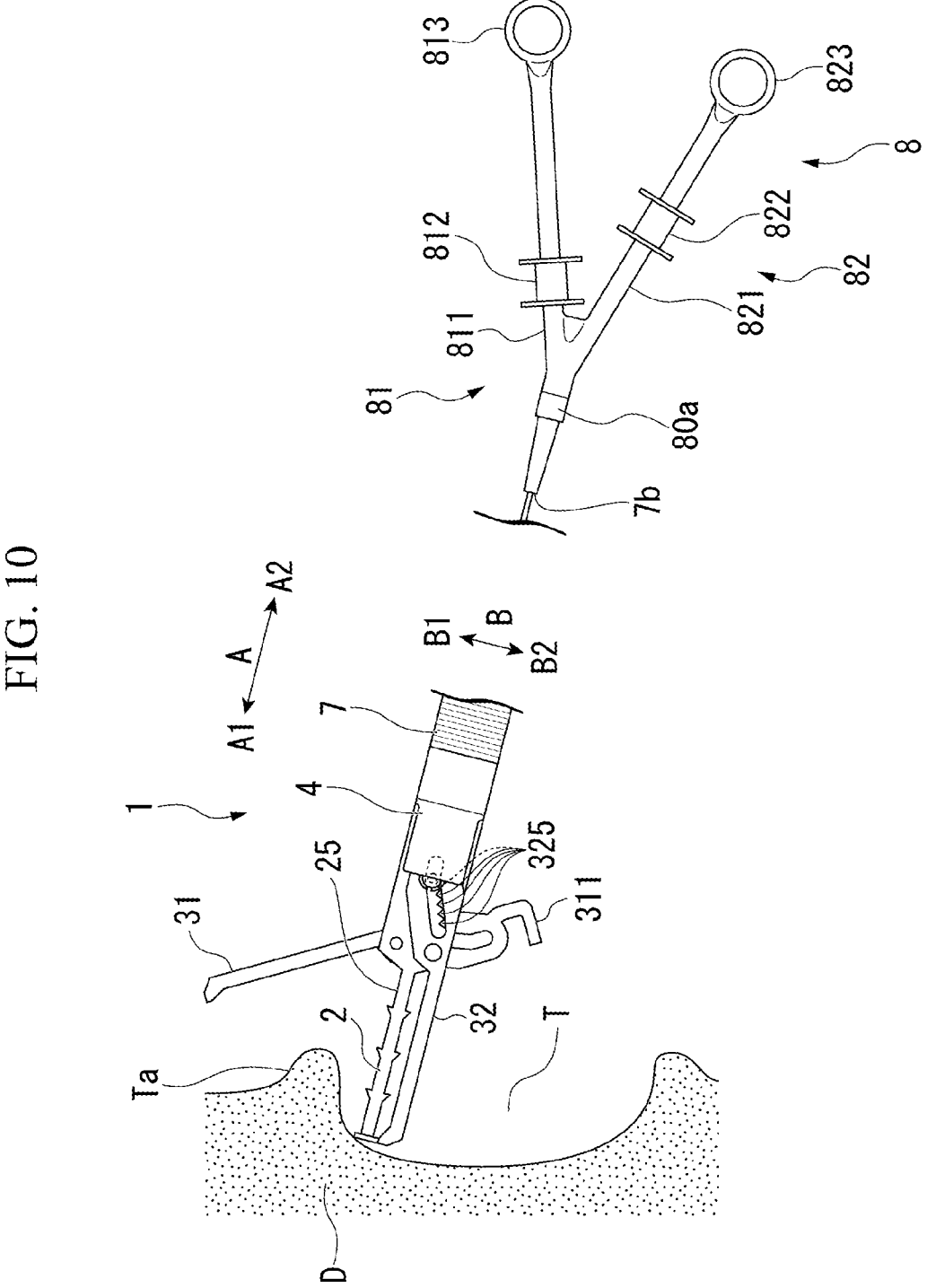
FIG. 10 is a schematic view showing an example of an operation of a treatment to the tissue using the clip.
Figure 11:
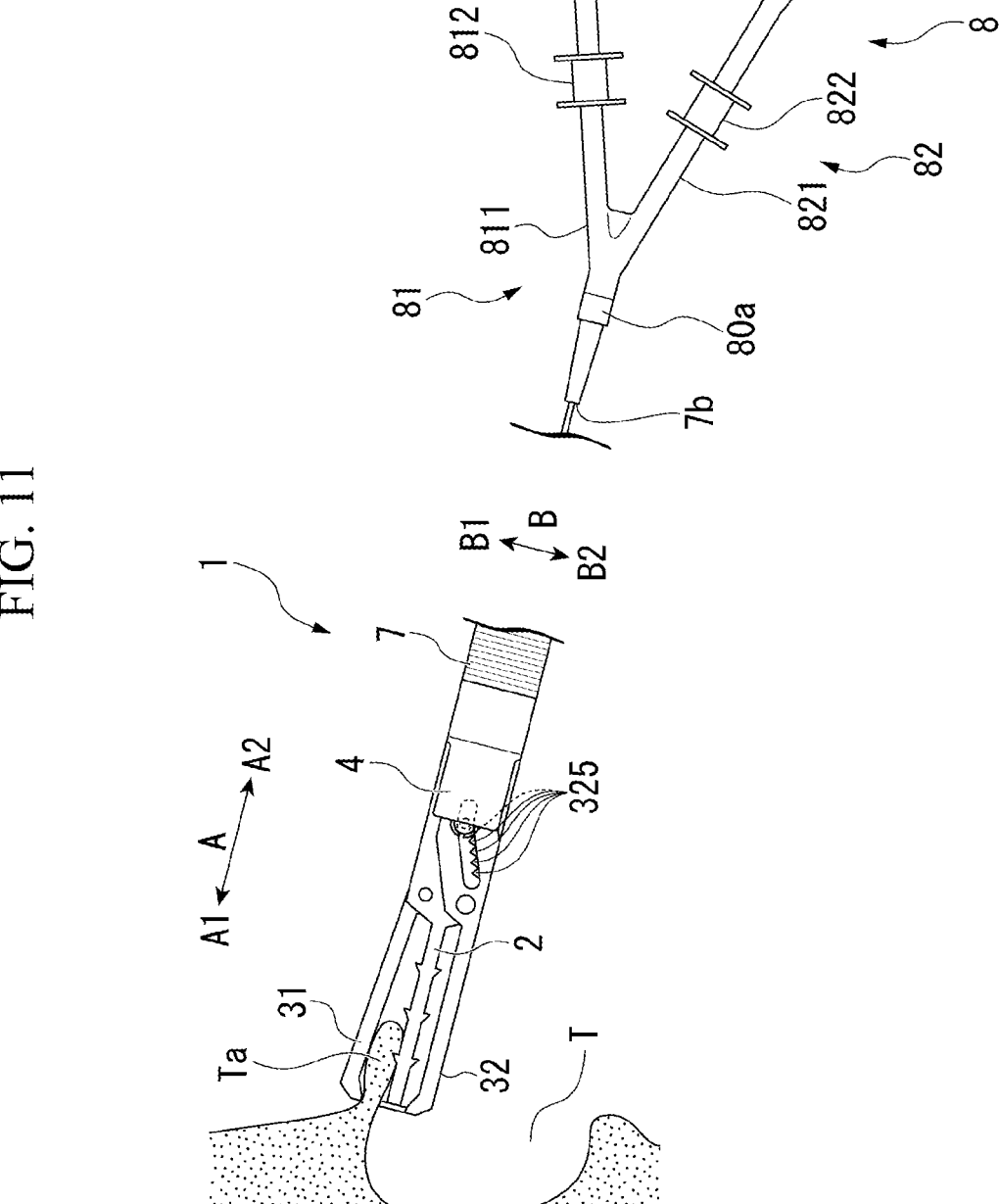
FIG. 11 is a schematic view showing an example of an operation of the treatment to the tissue using the clip.
Figure 12:
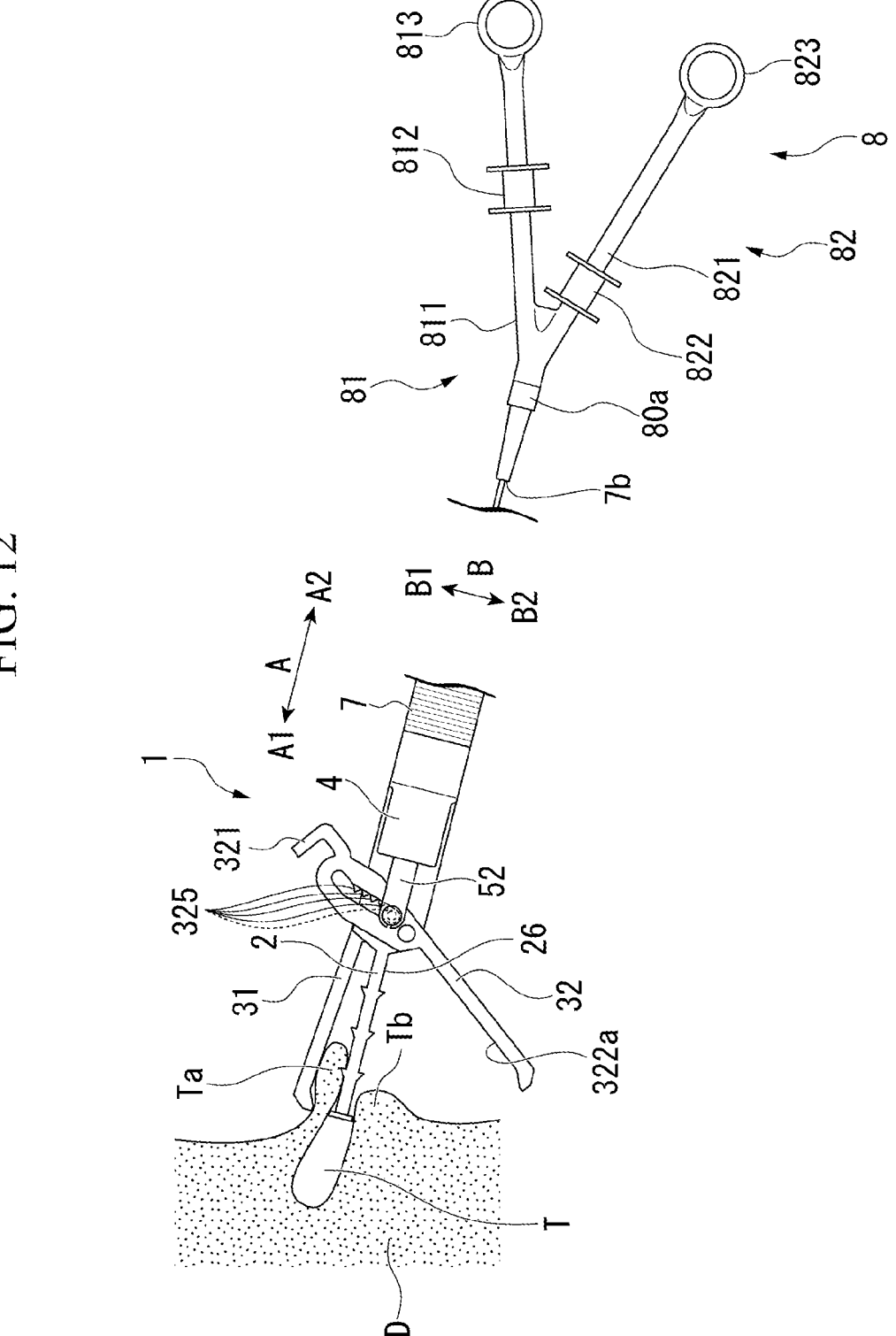
FIG. 12 a schematic view showing an example of an operation of the treatment to the tissue using the clip.
Figure 13:
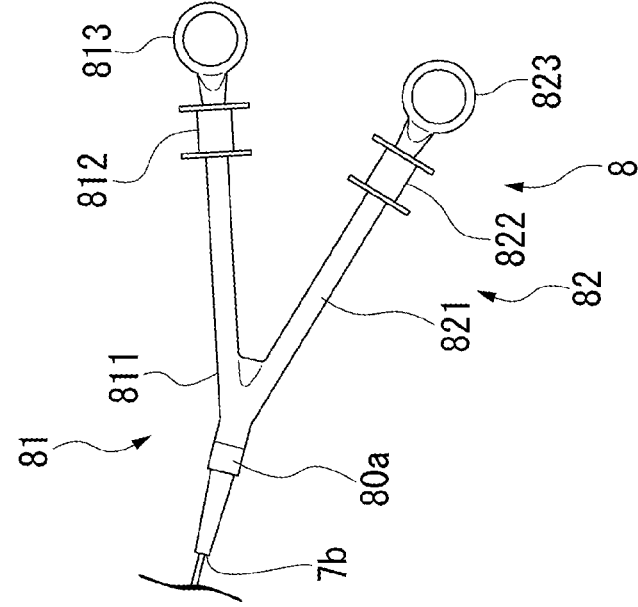
FIG. 13 is a schematic view showing an example of an operation of the treatment to the tissue using the clip.

FIG. 10 is a view schematically showing a state in which the first outer arm 31 of the treatment portion 1 of the clip device 100 is opened and the treatment portion 1 is brought to approach the tissue to be gripped. FIG. 11 is a view schematically showing a state in which the first outer arm 31 of the treatment portion 1 of the clip device 100 is closed and the tissue is gripped. FIG. 12 is a view schematically showing a state in which the first outer arm 31 of the treatment portion 1 of the clip device 100 grips tissue while the second outer arm 32 is opened and the treatment portion 1 is brought to approach the tissue to be gripped. FIG. 13 is a view schematically showing a state in which the second outer arm 32 of the treatment portion 1 of the clip device 100 is closed and the treatment portion 1 is deployed from the clip device 100 in a state in which the treatment portion 1 grips the tissue.

(Preparation)

As a preparation, an operator identifies a wound in a body tissue. More specifically, the operator inserts an insertion portion of an endoscope into the digestive tract of the esophagus, stomach, duodenum, large intestine, or the like through a natural orifice of the lumen (for example, the mouth of the patient), and identifies the defect T formed in a hole shape in the tissue D in the lumen as the treatment target while observing an image obtained by the imaging portion of the endoscope.

(Insertion Operation)

The operator inserts the clip device 100 into the channel of the endoscope, and protrudes the clip device 100 from the distal end opening of the working channel of the endoscope. The operator moves the treatment portion 1 provided on the distal end side A1 of the clip device 100 to the vicinity of the defect T.

(Arrangement Operation)

As shown in FIG. 10, the operator moves the first pulling member 51 to the distal end side A1 by pushing and advancing the first slider 812 of the first operation portion main body 811 in the longitudinal direction A. Thus, when the first slide pin 511 connected to the first pulling member 51 is advanced, the first outer arm 31 is rotated around the first rotation pin 211 as a rotation center. More specifically, the first outer arm 31 is rotated toward the first side B1 in the open-close direction B such that the first arm portion 312 at the distal end side A1 is separated from the central arm 2. As a result, the first outer arm 31 is opened with respect to the central arm 2 such as to be able to grip a first portion Ta of the defect T as the treatment target. In this arrangement step, the operator moves the first pulling member 51 toward the distal side A1 such that the first slide pin 511 rides over the plurality of teeth 315 formed in the first slide slot 310 while moving to the distal end side along the first slide slot 310 of the first outer arm 31.

In this state, the operator moves the first outer arm 31 and the central arm 2 in the open state toward the first portion Ta of the defect T to be gripped, and places the first portion Ta between the first outer arm 31 and the central arm 2.

(Gripping Operation)

In FIG. 11, when the operator has confirmed that the first portion Ta of the defect T is located between the first outer arm 31 and the central arm 2, the operator moves the first pulling member 51 to the proximal side A2 by pulling the first slider 812 of the first operation portion 81. Thus, when the first slide pin 511 connected to the first pulling member 51 is retracted, the first arm portion 312 of the first outer arm 31 is rotated to the second side B2 of the open-close direction B toward the central arm 2. As a result, the first outer arm 31 enters the closed state with respect to the central arm 2 to grip the first portion (first location) Ta of the defect T as the treatment target.

In the process when the operator pulls the first slider 812 to the proximal end side A2, the first engaging portion 311 formed on the proximal end side A2 of the first outer arm 31 also rotates in the open-close direction B around the first rotation pin 211 as a rotation center. As a result, the first engaging portion 311 enters the groove portion 41 formed in the clip holder 4 and is accommodated within the clip holder 4. As a result, the first portion Ta of the defect T is gripped by the first outer arm 31 and the central arm 2. During this process, when the operator moves the first pulling member 51 to the proximal side A2, the first slide pin 511 moves toward the proximal end side along the first slide slot 310 of the first outer arm 31 while the first slide pin 511 engages with either of the plurality of teeth 315 formed in the first slide slot 310. In this state, the advancement and retraction of the first slide pin 511 along the first slide slot 310 is restricted by the plurality of teeth 315 formed on the first slide slot 310. Accordingly, even if the operator does not maintain the state in which the first slider 812 is pulled toward the proximal side A2, the state in which the first portion Ta of the defect T is gripped by the first outer arm 31 and the central arm 2 is maintained. During the process, the operator may adjust the relative positional relationship of the first slide pin 511 and the plurality of teeth 315 such as to appropriately adjust the gripping force for gripping the first portion Ta of the defect T as the treatment target. More specifically, the gripping force is adjusted to a degree such that the first portion Ta of the defect T as the treatment target does not slip off from the gap between the first outer arm 31 and the central arm 2 and it is possible to prevent the gripping force from being excessively large to damage the first portion Ta of the defect T. However, the operator may advance the first outer arm 31 and transition the first outer arm 31 into the open state with respect to the central arm 2 such as to release and grip the first portion Ta of the defect T by operating the operation portion 8 again.

(Traction Operation)

In FIG. 12, while the state in which the first portion Ta of the defect T is gripped by the first outer arm 31 and the central arm 2 is maintained, the operator moves the entire treatment portion 1 to the vicinity of the second portion Tb of the defect T as a ligation target to which the first portion Ta of the defect T is ligated. In this process, the closed state between the first outer arm 31 and the central arm 2 is maintained by the first slide pin 511 engaging with the plurality of teeth 315 even without any operation by the operator.

(Arrangement Operation)

When the operator has confirmed that the treatment portion 1 reaches to the vicinity of the second portion Tb of the defect T, the operator moves the second pulling member 52 toward the distal end side A1 by pushing and advancing the second slider 822 of the second operation portion 82 in the longitudinal direction A. Accordingly, as shown in FIG. 12, when the second slide pin 521 connected to the second pulling member 52 is advanced, the second outer arm 32 is rotated around the second rotation pin 221 as a rotation center. More specifically, the second outer arm 32 is rotated toward the second side B2 in the open-close direction B such that the second arm portion 322 at the distal end side is separated from the central arm 2. As a result, the second outer arm 32 is in the open state with respect to the central arm 2, and it is possible to grip the second portion Tb of the defect T as the treatment target.

In this state, the operator moves the second outer arm 32 and the central arm 2 in the open state toward the second portion Tb of the defect T to be gripped, and places the second portion Tb of the defect T between the second outer arm 32 and the central arm 2.

(Gripping Operation)

As shown in FIG. 13, when the operator has confirmed that the second portion Tb of the defect T is located between the second outer arm 32 and the central arm 2, the operator moves the second pulling member 52 to the proximal side A2 by pulling the second slider 822 of the second operation portion 82. Thus, when the second slide pin 521 connected to the second pulling member 52 is retracted, the second arm portion 322 of the second outer arm 32 is rotated toward the first side B1 in the open-close direction B toward the central arm 2. As a result, the second outer arm 32 enters the closed state with respect to the central arm 2 to grip the second portion Tb of the defect T as the treatment target.

In the process in which the operator pulls the second slider 822 to the proximal end side A2, the second engaging portion 321 formed on the proximal end side A2 of the second outer arm 32 is also rotated around the second rotation pin 221 as the rotation center in the open-close direction B. As a result, the second engaging portion 321 enters the groove 41 formed in the clip holder 4 to be accommodated within the clip holder 4. As a result, the second portion Tb of the defect T is gripped by the second outer arm 32 and the central arm 2. In this process, when the operator moves the second pulling member 52 to the proximal side A2, the second slide pin 521 is engaged with either of the plurality of teeth 325 formed in the second slide slot 320 while moving to the proximal end side along the second slide slot 320 of the second outer arm 32. In this state, the advancement and retraction of the second slide pin 521 along the second slide slot 320 is restricted by the plurality of teeth 325 formed on the second slide slot 320. Therefore, even if the operator does not maintain the state in which the second slider 822 is pulled toward the proximal side A2, the second portion Tb of the defect T is maintained in a state of being gripped by the second outer arm 32 and the central arm 2. In this process, by adjusting the relative positional relationship between the second slide pin 521 and the plurality of teeth 325 by the operator, the gripping force for gripping the second portion Tb of the defect T as the treatment target can be appropriately adjusted. More specifically, it may be preferable that the gripping force is adjusted to the degree such that the second portion Tb of the defect T as the treatment target does not slip off from the gap between the second outer arm 32 and the central arm 2 and it is possible to prevent the gripping force from being excessively large to damage the second portion Tb of the defect T. However, the operator may advance the second outer arm 32 and transition the second outer arm 32 into the open state with respect to the central arm 2 such as to release and then grip the second portion Tb of the defect T by operating the operation portion 8 again.

Thereafter, when the operator retracts the first slider 812 of the operation portion 8 further to the proximal end side A2 in the longitudinal direction A, the clip holder 4 is configured to make the first engaging portion 311 of the first outer arm 31 to be engaged inside the clip holder 4 and the first outer arm 31 is locked to be impossible to open. When the second slider 822 of the operation portion 8 is retracted further to the proximal end side A2 in the longitudinal direction A, the clip holder 4 is configured to make the second engagement portion 321 of the second outer arm 32 to be engaged inside the clip holder 4 and the second outer arm 32 is locked to be impossible to open.

(Deployment Operation)

By the above-described treatment, as shown in FIG. 13, the first portion Ta and the second portion Tb of the defect T as the treatment target are gripped by the treatment portion 1. In this state, the operator moves the first pulling member 51 and the second pulling member 52 to the proximal side A2 by further pulling the first slider 812 of the first operation portion 81 and the second slider 822 of the second operation portion 82 to the proximal side A2.

In the present example, the first pulling member 51 and the second pulling member 52 are detachably engaged with the first slide pin 511 and the second slide pin 521, respectively. For example, when the operator pulls the first pulling member 51 toward the proximal end side A2, the notch portion 512 of the first pulling member 51 is deformed or broken, and the first slide pin 511 may be pulled out of the first slide pin hole 510 and disengaged therefrom. Also, when the operator pulls the second pulling member 52 to the proximal end side A2, the notch portion 522 of the second pulling member 52 is deformed or broken, and the second slide pin 521 may be pulled out of the second slide pin hole 520 to release the engagement. The specific configurations of the engagement between the first pulling member 51 or the second pulling member 52 and the first slide pin 511 or the second slide pin 521 is not limited to the present example.

When the force by which the operator moves the first pulling member 51 and the second pulling member 52 to the proximal side A2 exceeds a predetermined value, as described above, the engagement between the first pulling member 51 or the second pulling member 52 and the first slide pin 511 or the second slide pin 521 is released. As a result, the treatment portion 1 of the clip device 100 is deployed in the lumen in the state in which the first portion Ta of the defect T is gripped by the first outer arm 31 and the central arm 2, and the second portion Tb of the defect T is gripped by the second outer arm 32 and the central arm 2.

Thereafter, the operator operates the operation portion 8 of the clip device 100 to remove the sheath 7 to the outside of body of the patient, thereby finishing the treatment for the treatment target.

In the present example, according to the above-described configuration, the treatment portion 1 of the clip device 100 may close the defect T of the tissue D as the treatment target.

[Effect of Clip Device 100]

According to the clip device 100 of the present example, in the gripping operation and the traction operation of gripping the defect T as the treatment target, even if the operator does not maintain the state of pulling the first slider 812 or the second slider 822 toward the proximal side A2, it is possible to maintain the state in which the defect T as the treatment target is gripped by the first outer arm 31 or the second outer arm 32 and the central arm 2. In other words, according to the clip device 100 of the present example, even if the operator does not operate the operation portion 8, that is, even if the operator does not operate the handle, the force by which the pair of outer arms 3 and the central arm 2 of the treatment portion 1 grip the defect T is appropriately maintained, it is possible to prevent the tissue from slipping off from the arms such that the tissue can be gripped reliably.

In the present example, a ratchet structure is formed by the plurality of teeth 315 or the plurality of teeth 325 formed in the first slide slot 310 of the first outer arm 31 or the second slide slot 320 of the second outer arm 32, and the plurality of teeth 231 formed in the engaging groove 23 of the central arm 2. According to this configuration, the pair of outer arms 3 and the central arm 2 can be moved stepwise by the operation of the operator. The force of making the first slide pin 511 or the second slide pin 521 to ride over the plurality of teeth 315 or the plurality of teeth 325 is set to be smaller than the force for releasing the engagement between the first pulling member 51 or the second pulling member 52 and the first slide pin 511 or the second slide pin 521, that is, the force for deploying the treatment portion 1 of the clip device 100 in the lumen.

In the present example, the plurality of teeth 231 provided in the central arm 2, or the plurality of teeth 315, 325 together with the first slide pin 511 and the second slide pin 521 provided in the pair of outer arms 3 provide a gripping force adjustment structure configured to adjust the gripping force for gripping the defect T of the biological tissue as the treatment target. In the present example, the central arm 2, the pair of outer arms 3, and the gripping force adjustment structure provides a gripping structure for gripping the biological tissue.

In the present example, a release structure for opening and closing the above-described gripping structure is configured by the pair of pulling members 5 and the pair of operation wires 6. The pair of pulling members 5 and the pair of operation wires 6 function as a force transmitter device for transmitting the force by the operator to the gripping structure. As described above, the pair of pulling members 5 are detachably connected to the pair of outer arms 3 and the central arm 2.

The first example of the present disclosure has been described above in detail with reference to the figures; however, the specific configuration is not limited to this example, and design changes or the like within a range not deviating from the spirit of the present example are also included. In addition, it is possible to appropriately combine and configure the configuration elements shown in the above-described example, the following examples, and the modified examples.

First Modified Example

Figure 14:
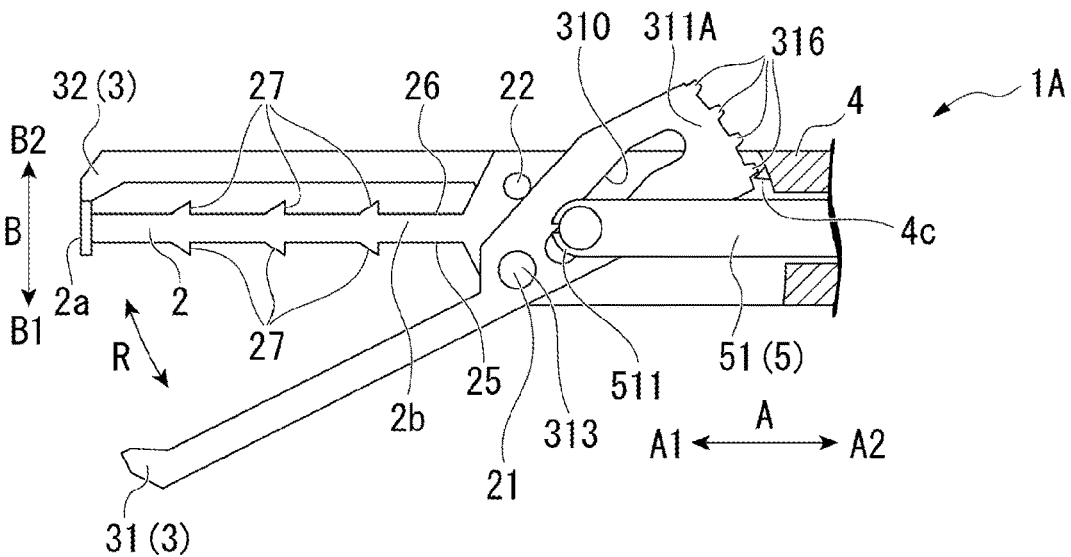
FIG. 14 is a side view showing an example of a configuration of a treatment portion of a clip according to a first modified example of the present disclosure.
Figure 15:
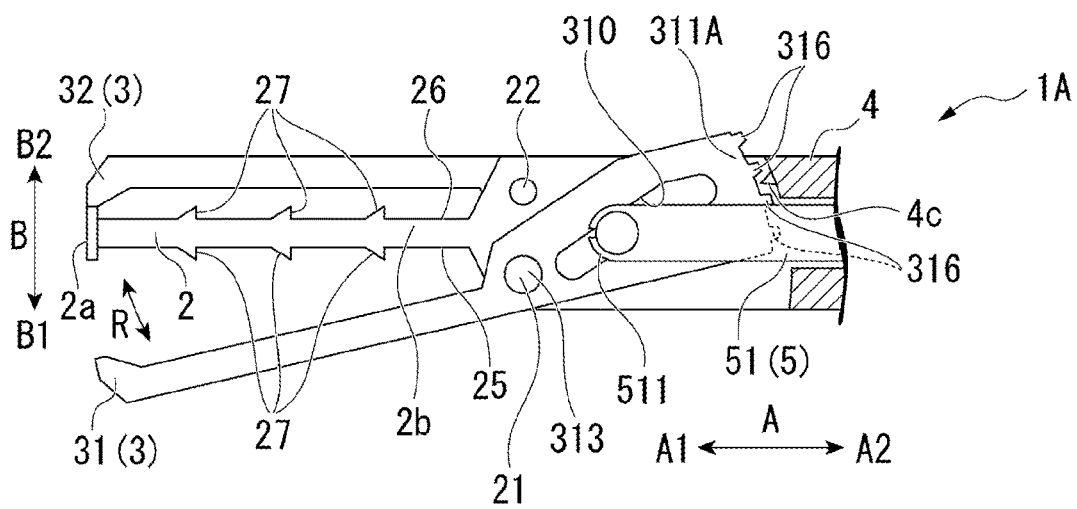
FIG. 15 is a side view showing an example of the configuration of the treatment portion of the clip according to the present modified example.
Figure 16:
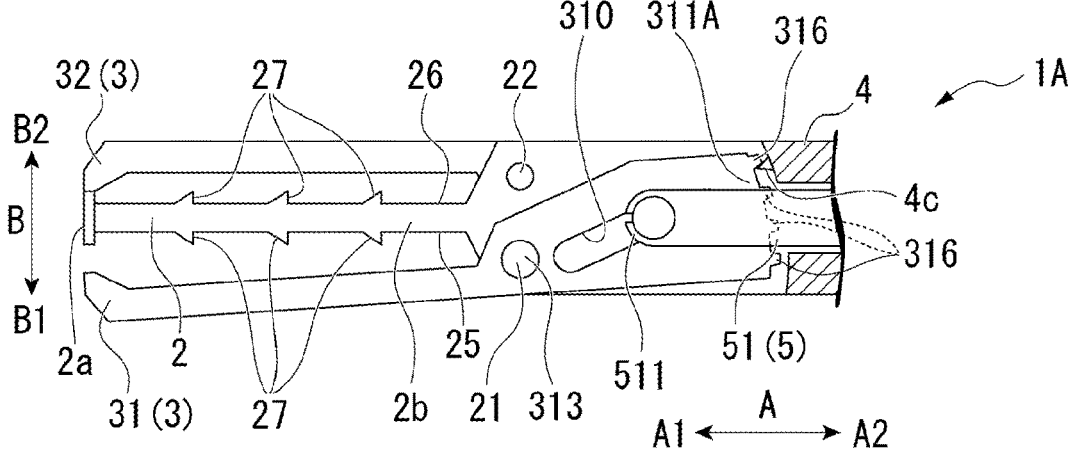
FIG. 16 is a side view showing an example of the configuration of the treatment portion of the clip according to the present modified example.

Hereinafter, a configuration of a treatment portion 1A of the clip device 100 according to the first modified example of the present embodiment will be described referring to FIG. 14 to FIG. 16. FIG. 14 to FIG. 16 are views of showing the configuration of the treatment portion 1A according to the present modified example by taking the open-close operation of the first outer arm 31 of the treatment portion 1A as an example. FIG. 14 is a view showing the open state of the first outer arm 31 and the central arm 2 of the treatment portion 1A. FIG. 15 is a view showing an operation in which the first outer arm 31 is rotated inwardly in the direction R to approach the central arm 2. FIG. 16 is a view showing a closed state of the first outer arm 31 and the central arm 2.

As shown in FIG. 14 to FIG. 16, when compared with the first example described above, in the treatment portion 1A according to the present modified example, instead of the plurality of teeth 315, 325 formed in the slide slots (first slide slot 310 and second slide slot 320) of the pair of outer arms 3, and the plurality of teeth 231 formed in the engaging groove 23 of the central arm 2, a plurality of teeth 316 are formed in the proximal end portion 311A of the first outer arm 31 and the proximal end portion of the second outer arm 32.

As shown in FIG. 14, instead of the elastic member such as the first engaging portion 311 according to the first example described above, the proximal end 311A of the first outer arm 31 is formed with a substantially arcuate proximal surface. The proximal end 311A does not have the elasticity, and the plurality of teeth 316 are formed to protrude from the proximal end surface toward the clip holder 4. A protrusion (stopper, matching member) 4c configured to engage with each of the plurality of teeth 316 is formed on the distal end surface of the clip holder 4 such as to correspond to the plurality of teeth 316 formed on the proximal end portion of the proximal end 311A. In this modified example, the plurality of teeth 316 formed on the proximal end surface of the proximal end 311A of the first outer arm 31 and the protrusion 4c formed on the distal end surface of the clip holder 4 can engage with each other. The protrusion 4c formed on the distal end surface of the clip holder 4 may restrict the movement of the plurality of teeth 316 in a state of engaging with the plurality of teeth 316. The other configurations of the treatment portion 1A of the clip device 100 is the same as the configuration according to the first example described above, and therefore the description thereof is omitted.

As shown in FIG. 14 through FIG. 16, when the operator operates to retract the first pulling member 51 to the proximal side, the first slide pin 511 moves along the first slide slot 310 of the first outer arm 31 toward the proximal side. As the movement of the first slide pin 511 toward the proximal end side, the proximal end portion 311A formed on the proximal end side A2 of the first outer arm 31 is rotated in the open-close direction B around the first rotation pin 211 as the rotation center, that is, the proximal end portion 311A is rotated inwardly in the radial direction R.

When the proximal end portion 311A formed on the proximal end side A2 of the first outer arm 31 is rotated inwardly in the radial direction R, the protrusion 4c and the plurality of teeth 316 relatively move to each other in the radial direction R such that the protrusion 4c rides over the plurality of teeth 316. The protrusion 4c and each of the plurality of teeth 316 move (rotate) relative to each other such that the relative positional relationship changes in a stepwise manner. Therefore, the relative open-close relationship between the first outer arm 31 and the central arm 2 also changes stepwise. Further, when the protrusion 4c rides over either of the plurality of teeth 316 and is engaged with either of the plurality of teeth 316, the relative positional relationship between the protrusion 4c and the tooth 316 does not change unless an external force is applied by the operation of the operator. That is, in this state, the open-close relationship between the first outer arm 31 and the central arm 2 is maintained even if the operator does not operate the operation portion 8.

As shown in FIG. 16, the protrusion 4c is moved relative to the plurality of teeth 316 such that the first outer arm 31 is rotated such as to approach the central arm 2, and the defect T of the biological tissue as the treatment target may be gripped. For example, the first portion Ta of the defect T may be gripped by the first outer arm 31 and the central arm 2 which approach each other to enter the substantial closed state (see FIG. 16) using the treatment portion 1A of the clip device 100 according to the present modified example. In this state, even if the operator does not maintain the state in which the first slider 812 is pulled toward the proximal side A2, the open-close state of the first outer arm 31 and the central arm 2 is maintained. That is, according to the treatment portion 1A of the clip device 100 according to the present modified example, by the stepwise relative movement between the protrusion 4c provided in the clip holder 4 and the plurality of teeth 316 provided in the proximal end portion 311A of the first outer arm 31, the gripping force for gripping the defect T of the biological tissue by the first outer arm 31 and the central arm 2 may be changed stepwise. Furthermore, even if the operator does not operate the operation portion 8 to maintain the state in which the first slider 812 is pulled toward the proximal end side A2, the relative positional relationship between the protrusion 4c and the plurality of teeth 316 is not changed such that the open-close relationship between the first outer arm 31 and the central arm 2 is maintained.

In the treatment portion 1A of the clip device 100 according to the present modified example, the second outer arm 32 has the same configuration as that of the first outer arm 31. Therefore, the duplicate description of the configuration of the second outer arm 32 is omitted. In the treatment portion 1A of the clip device 100 according to the present modified example, the plurality of teeth 316 formed on the proximal end 311A of the first outer arm 31 and the protrusion 4c provided on the distal end surface of the clip holder 4 provide the gripping force adjustment structure configured to adjust the gripping force for gripping the defect T of the biological tissue as a treatment target.

As shown in FIG. 14 through FIG. 16, an example of the configuration of the treatment portion 1A of the clip device 100 according to the present modified example has been described; however, the present disclosure is not limited thereto. For example, a configuration of the treatment portion 1A in which a protrusion is formed in the first outer arm 31 and a plurality of corresponding teeth are formed in the distal end surface of the clip holder 4 may be adopted. Furthermore, for example, in the treatment portion 1A of the clip device 100, the plurality of teeth 316 may be formed only on a partial portion of the proximal end surface of the proximal end 311A of the first outer arm 31. More specifically, even it is not shown in the figures, the plurality of teeth 316 may be formed only on a portion of the proximal end surface of the proximal end 311A of the first outer arm 31 located outside in the radial direction R. According to such a configuration, until the protrusion 4c formed on the distal end surface of the clip holder 4 rides over either of the plurality of teeth 316 to engage thereto, it is possible to freely open and close the first outer arm 31 and the central arm 2 freely. That is, according to such a configuration, the operator may easily grip the first portion Ta of the defect T of the tissue as the treatment target.

In a case of using the treatment portion 1A of the clip device 100 according to the present modified example, the operator may perform the treatment of ligating the defects T of the biological tissue as the treatment target by the same procedures as in the first example described above. More specifically, for example, when the operator has confirmed that the first portion Ta of the defect T is located between the first outer arm 31 and the central arm 2 in the gripping step, the operator moves the first pulling member 51 to the proximal side A2 by pulling the first slider 812 of the first operation portion 81. Thus, as shown in FIG. 15 and FIG. 16, when the first slide pin 511 connected to the first pulling member 51 is retracted, the first arm portion 312 located at the distal end side of the first outer arm 31 is rotated toward the central arm 2 in the second side B2 of the open-close direction B while the proximal end 311A is rotated in the first side B1 of the open-close direction B with respect to the protrusion 4c located on the distal end surface of the clip holder 4. As a result, the first outer arm 31 enters the closed state with respect to the central arm 2 to grip the first portion Ta of the defect T as the treatment target. During this process, the relative positional relationship between the protrusion 4c and the plurality of teeth 316 is changed stepwise such that the gripping force by the first outer arm 31 and the central arm 2 is also changed stepwise.

Second Modified Example

Hereinafter, referring to FIG. 17 through FIG. 19, a configuration of a treatment portion 1B of the clip device 100 according to a second modified example of the present example will be described. The treatment portion 1B of the clip device 100 according to the present modified example is different from the above-described first example in the aspect of the engagement between the pulling member and the outer arm.

Figure 17:
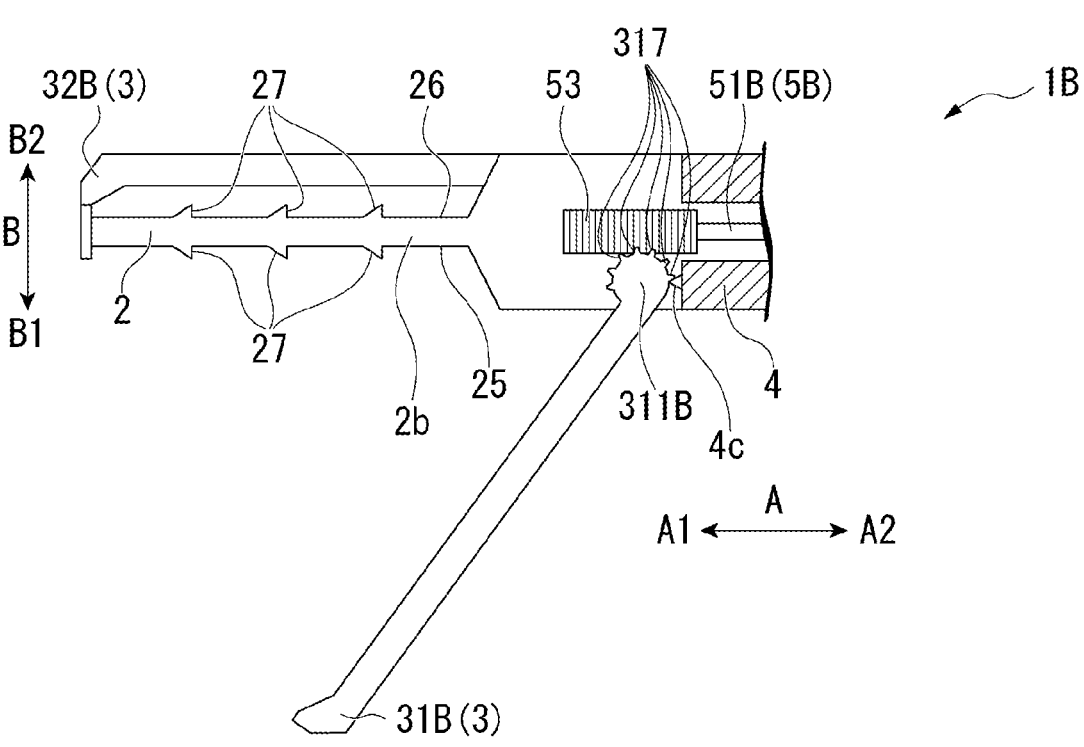
FIG. 17 is a side view showing an example of a configuration of a treatment portion of a clip according to a second modified example of the present disclosure.

As shown in FIG. 17, a first outer arm 31B according to the present modified example, instead of the first slide slot 310 formed in the first outer arm 31 according to the first example described above, a configuration in which a plurality of teeth 317 is formed in a circumferential direction of the proximal end portion 311B having a proximal end surface formed in a circular shape is adopted. A protrusion (stopper, matching member) 4c corresponding to the plurality of teeth 317 is formed on the distal end surface of the clip holder 4 according to the present modified example. Furthermore, at the distal end side of the first pulling member 51B according to the present modified example, a gear 53 formed to mesh with the plurality of teeth 317 formed on the proximal end portion 311B of the first outer arm 31B is formed. In the treatment portion 1B of the clip device 100 according to this modified example, the gear 53 provided on the distal end side of the pulling member 51B and the plurality of teeth 317 formed on the proximal end portion 311B of the first outer arm 31B configure a rack gear structure.

Figure 18:
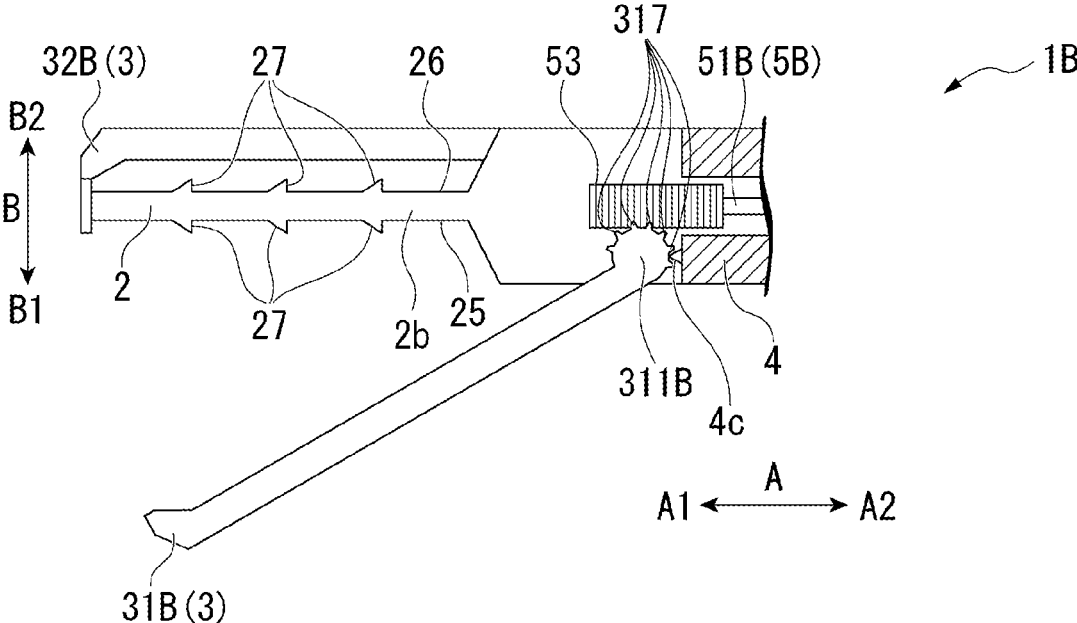
FIG. 18 is a side view showing an example of the configuration of the treatment portion of the clip according to the present modified example.
Figure 19:
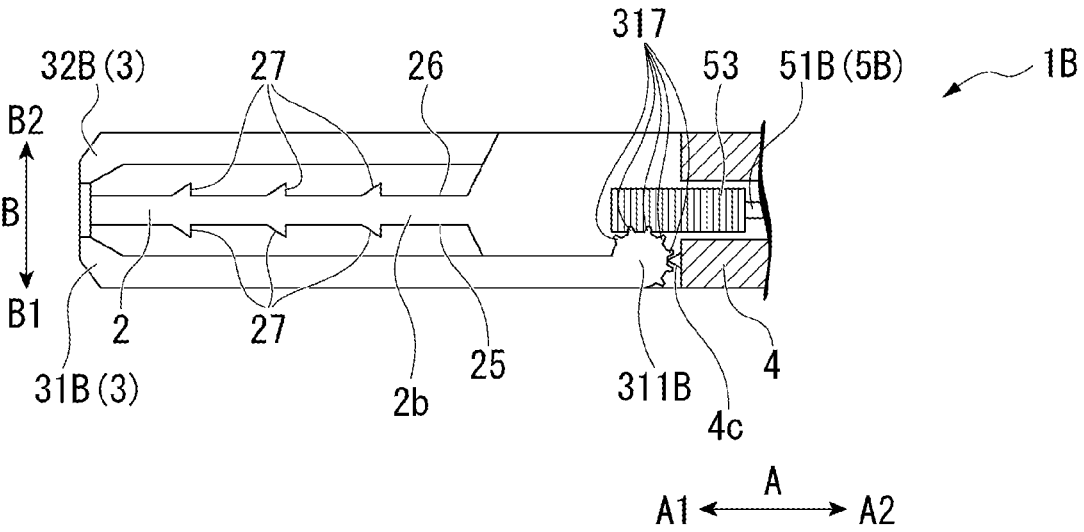
FIG. 19 is a side view showing an example of the configuration of the treatment portion of the clip according to the present modified example.

According to the treatment portion 1B of the clip device 100 according to the present modified example, as shown in FIG. 17 through FIG. 19, the gear 53 provided at the distal end side of the pulling member 5B and the plurality of teeth 317 formed on the proximal end portion 311B of the first outer arm 31B are engaged with each other such as to mesh with each other. According to the treatment portion 1B of the clip device 100 according to the present modified example, when the operator advances and retracts the pulling member 5B along the longitudinal direction A, the gear 53 and the plurality of teeth 317 are engaged with each other such that the linear movement of the pulling member 5B along the longitudinal direction A is converted into the rotational operation of the proximal end portion 311B of the first outer arm 31B. More specifically, when the operator advances the pulling member 5B to the distal end side A1 in the longitudinal direction A, the first outer arm 31B is rotated to the first side B1 in the open-close direction B such that the first outer arm 31B and the central arm 2 are in the open state. On the other hand, when the operator retracts the pulling member 5B to the proximal side in the longitudinal direction A, the first outer arm 31B is rotated in the second side B2 in the open-close direction B such that the first outer arm 31B and the central arm 2 enter the closed state.

In this process, by the relative movement between the protrusion 4c provided on the distal end surface of the clip holder 4 and the plurality of teeth 317 formed on the proximal end portion 311B of the first outer arm 31B, the protrusion 4c rides over either of the plurality of teeth 317 and enters the state of engaging with either of the plurality of teeth 317. According to the above-described configuration, the relative positional relation between the gear 53 and the plurality of teeth 317 may be changed stepwise with the advancement and retraction of the pulling member 5B along the longitudinal direction A. Each time when the protrusion 4c provided on the distal end surface of the clip holder 4 rides over either of the plurality of teeth 317, the first outer arm 31B rotates stepwise with respect to the central arm 2. In other words, in this process, the gripping force by the first outer arm 31B and the central arm 2 with respect to the defect T of the biological tissue as the treatment target varies stepwise corresponding to the change in the relative positional relationship between the first outer arm 31B and the central arm 2. In this modified example, the gears 53 and the plurality of teeth 317 may move relatively to each other in an interlocking manner. On the other hand, the protrusion 4c provided on the distal end surface of the clip holder 4 may restrict the movement of the plurality of teeth 317 in a state of engaging with the plurality of teeth 317.

In the case of using the treatment portion 1B of the clip device 100 according to the present modified example, the operator may perform the ligation treatment with respect to the defects T of the biological tissue as the treatment target in accordance with the same procedures as in the first example described above. That is, for example, when the operator has confirmed that the first portion Ta of the defect T is located between the first outer arm 31B and the central arm 2 in the gripping step, the operator moves the first pulling member 51B to the proximal side A2 by pulling the first slider 812 of the first operation portion 81. Thus, as shown in FIG. 17, FIG. 18, and FIG. 19, when the operator retracts the first pulling member 51B to the proximal end side A2, the first outer arm 31B is rotated toward the central arm 2 in the second side B2 of the open-close direction B while the proximal end portion 311B positioned on the distal end surface of the clip holder 4 is rotated in the first side B1 of the open-close direction B with respect to the protrusion 4c. As a result, the first outer arm 31B enters the closed state with respect to the central arm 2 to grip the first portion Ta of the defective T as the treatment target. In this process, the relative positional relationship between the protrusion 4c and the plurality of teeth 317 is changed stepwise such that the gripping force between the first outer arm 31B and the central arm 2 is also changed stepwise.

Second Example

Figure 20:
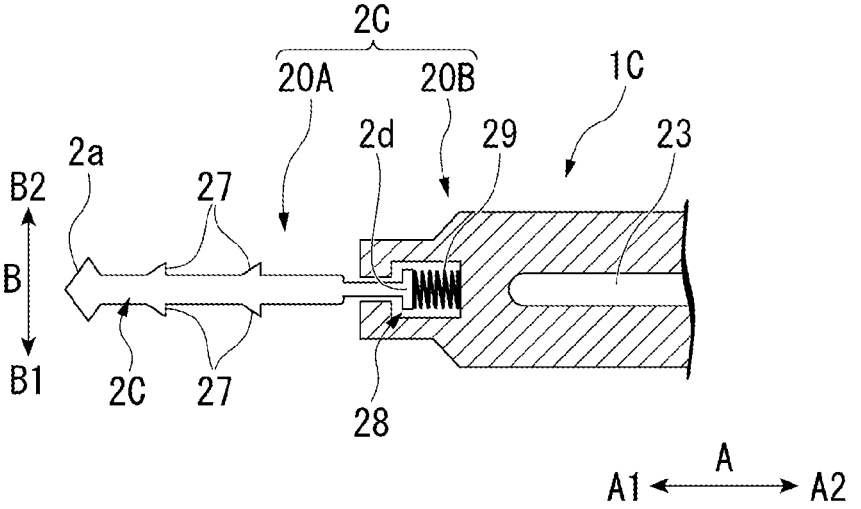
FIG. 20 is a partial cross-sectional view showing an example of a configuration of a central arm of a clip according to a second example of the present disclosure.
Figure 21:
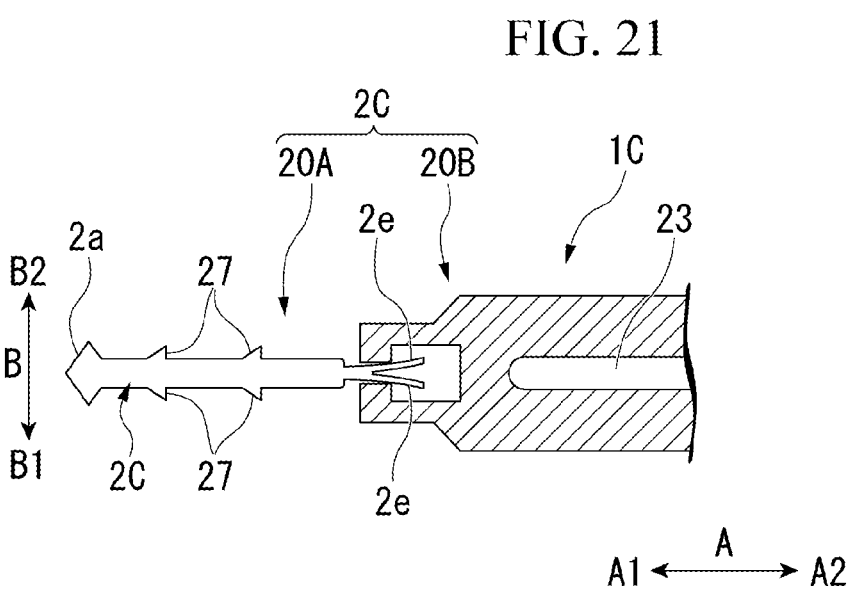
FIG. 21 is a partial cross-sectional view showing an example of a configuration of a central arm according to a modified example of the present disclosure.
Figure 22:
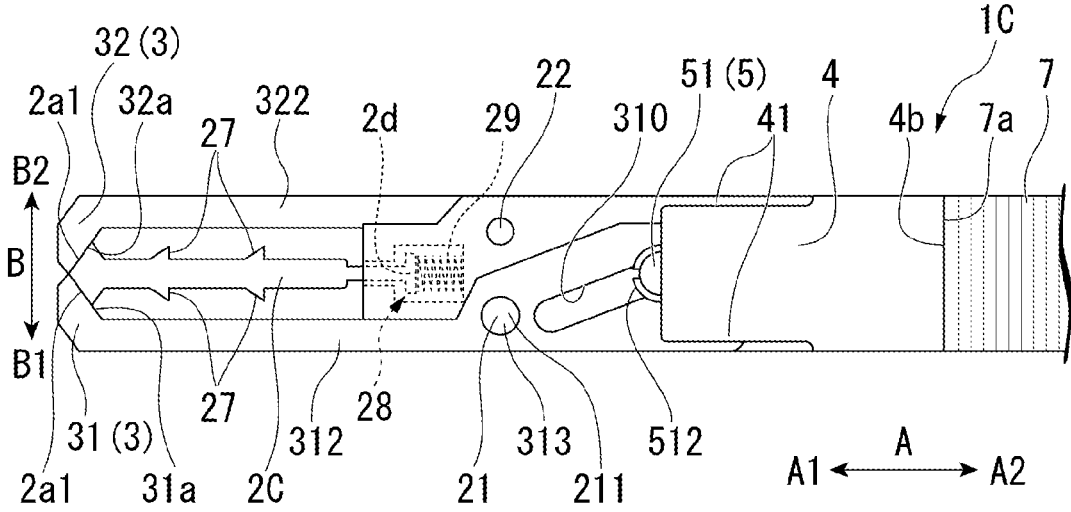
FIG. 22 is a schematic view showing an example of a configuration of a treatment portion of the clip according to the present disclosure.
Figure 23:
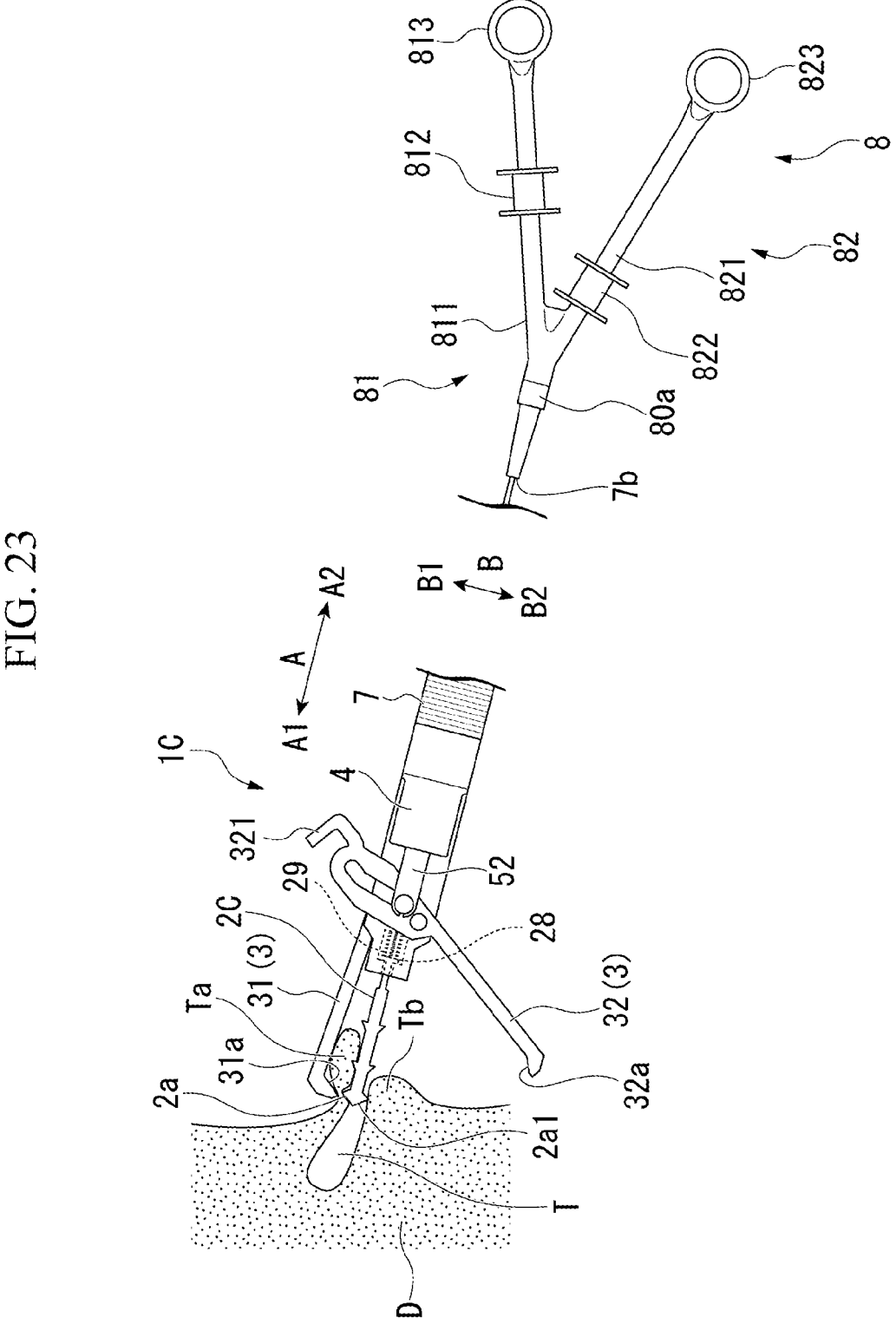
FIG. 23 is a schematic view showing an example of an operation of the treatment to the tissue using the clip.
Figure 24:
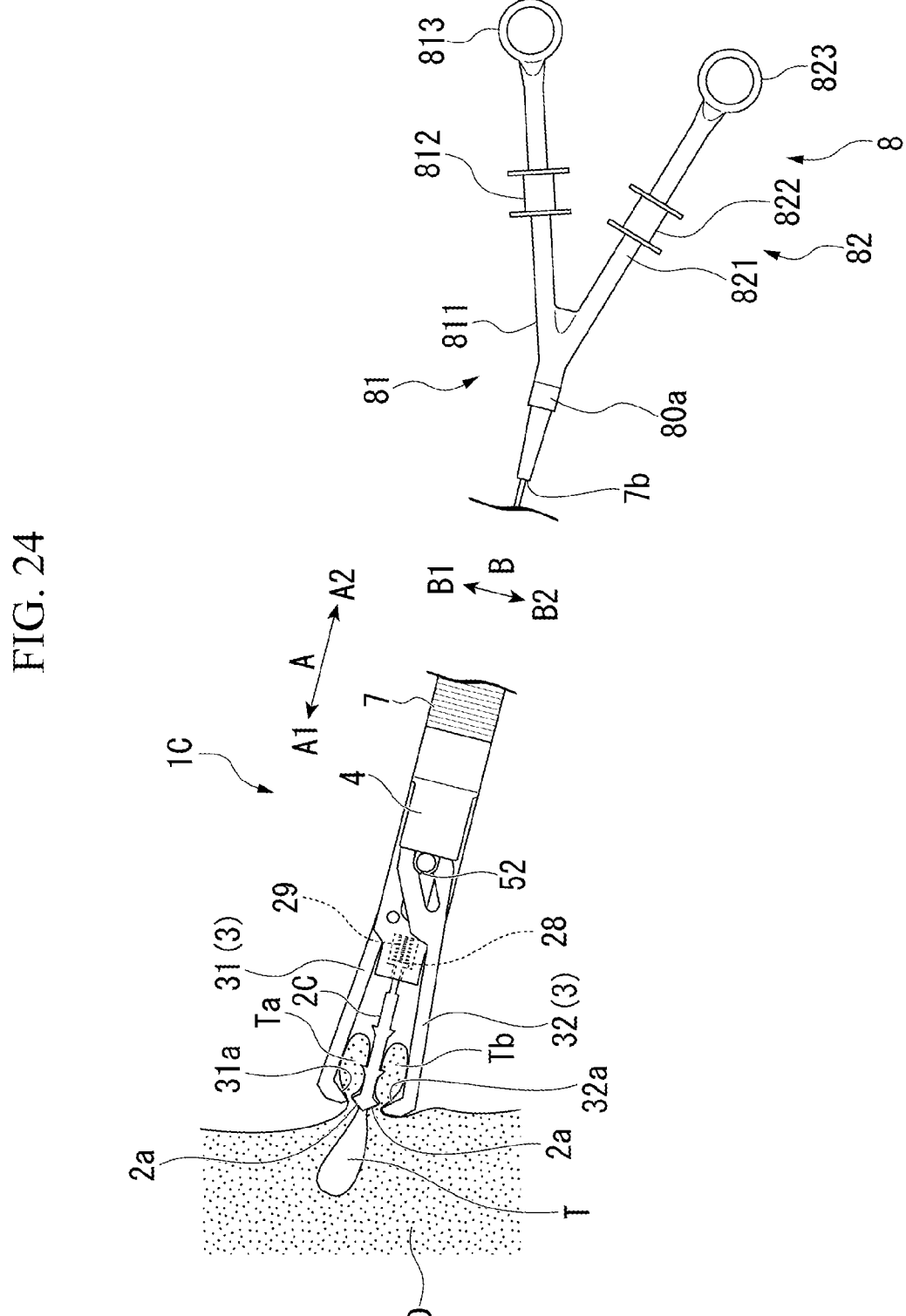
FIG. 24 is a schematic view showing an example of an operation of the treatment to the tissue using the clip.

Hereinafter, referring to FIG. 20 through FIG. 24, a configuration of a treatment portion 1C of the clip device 100 according to the second example of the present disclosure will be described. FIG. 20 is a view showing a configuration of a central arm 2C of the treatment portion 1C of the clip device 100 according to the present example. FIG. 21 is a view showing a modified example of the configuration of the central arm 2C. FIG. 22 is a view showing a configuration of the treatment portion 10 of the clip device 100 according to the present example. FIG. 23 and FIG. 24 are views showing a treatment with respect to the defect T of the biological tissue as the treatment target using the treatment portion 10 of the clip device 100 according to the present example.

The treatment portion 10 of the clip device 100 according to the present example is different from the treatment portion 1 of the clip device 100 according to the first example described above in that the treatment portion 1C includes an elastic member 29 provided to push out the central arm 2C toward the distal end side A1 in the longitudinal direction A. The elastic member 29 according to the present example may be configured of, for example, various conventional springs. As shown in FIG. 20, the central arm 2C according to the present example includes a rod portion 20A formed on the distal end side A1 and a connecting portion 20B formed on the proximal end side A2. In the connecting portion 20B of the central arm 2C, a space 28 for accommodating the elastic member 29 is formed. In the space 28, the distal end of the elastic member 29 is connected to the proximal end of the rod portion 20A of the central arm 2C and the proximal end thereof is fixed to an inner wall of the space 28. In the present example, the proximal ends of the elastic member 29 and the rod portion 20A are accommodated in the space 28 such that it is possible to restrict the radial movement generated when the elastic member 29 is bent. In the present example, it may be preferable that the elastic member 29 is provided at the proximal end side of the central arm 2C, that is, at a position being accommodated in the clip holder 4.

In FIG. 20, an example of the configuration of the central arm 2C according to the present example is shown; however, the configuration of the central arm according to the present example is not limited thereto. For example, as shown in FIG. 21, as a modified example of the configuration of the central arm 2C, instead of the elastic member 29, the rod portion 20A of the central arm 2C may be configured to have elasticity. As shown in FIG. 21, the rod portion 20A of the central arm 2C may have a pair of proximal end portions 2e that are biased to be separated from each other. The pair of proximal end portions 2e are biased to be separated from each other such as to apply a biasing force for pushing the rod portion 20A of the central arm 2C to the distal end side A1 in the longitudinal direction A, and the pair of proximal end portions 2e are engaged in the space 28 formed in the central arm 2C. Similar to the configuration shown in FIG. 20, the central arm 2C shown in FIG. 21 is configured to bias the rod portion 20A toward the distal end side A1 in the longitudinal direction A such as to push the rod portion 20A.

FIG. 22 is a view showing a configuration of a treatment portion 1C of the clip device 100 according to the present example. As shown in FIG. 22, the elastic member 29 in the treatment portion 1C of the clip device 100 according to the present example is accommodated in the space 28 formed in the central arm 2C. On the other hand, the distal ends of the first outer arm 31 and the second outer arm 32 of the treatment portion 1C according to the present example are located on the distal end side A1 of the distal end side than the central arm 2C. In other words, as shown in FIG. 22, when the first outer arm 31 or the second outer arm 32 and the central arm 2C are in the closed state, due to the biasing force of the elastic member 29, a distal end surface 2a1 of the central arm 2C abuts against an inner surface 31a of the distal end portion of the first outer arm 31 and an inner surface 32a of the distal end portion of the second outer arm 32. The other configurations of the treatment portion 1C of the clip device 100 according to the present example are generally similar the treatment portion 1 of the clip device 100 according to the first example described above.

FIG. 23 and FIG. 24 are views showing the ligation treatment with respect to the defect T of the biological tissue as the treatment target using the treatment portion 1C of the clip device 100 according to the present example. As shown in FIG. 23, in the gripping operation, the first portion Ta of the defective T is gripped by the first outer arm 31 and the central arm 2C. More specifically, the first portion Ta of the defect T is gripped between the inner surface 31a of the distal end portion of the first outer arm 31 and the distal end surface 2a1 of the central arm 2C. Since the elastic member 29 according to the present example biases the central arm 2C such as to push the central arm 2C toward the distal end side A1 in the longitudinal direction A, in this state, even if the operator unintentionally advances the first slider 812 of the operation portion 8 toward the distal end side A1 in the longitudinal direction A, the state in which the first portion Ta of the defect T is gripped by the first outer arm 31 and the central arm 2C is maintained. Furthermore, since the first portion Ta of the defect T is gripped between the inner surface 31a of the first outer arm 31 and the distal end surface 2a1 of and the central arm 2C, it is possible to prevent the tissue from being damaged by the sharp edges of the first outer arm 31 and the central arm 2C. The elastic member 29 is configured to allow the movement of the central arm 2C toward the proximal end side A2 in the longitudinal direction A. Therefore, it is possible to prevent the first portion Ta of the defect T from being gripped by the inner surface 31a of the distal end portion of the first outer arm 31 and the distal end surface 2*a*1 of the central arm 2C with an excessively large force.

As shown in FIG. 24, similar to the treatment using the treatment portion 1 of the clip device 100 according to the first example described above, when the operator retracts the second slider 822 of the operation portion 8 to the proximal end side A2 in the longitudinal direction A, the second outer arm 32 is rotated toward the first Side B1 in the open-close direction B with respect to the central arm 2C. Accordingly, the second portion Tb of the defect T is gripped between inner surface 32*a* of the distal end portion of the second outer arm 32 and the distal end surface 2*a*1 of the central arm 2C. Thereafter, even if the operator unintentionally advances the second slider 822 of the operation portion 8 toward the distal end side A1 in the longitudinal direction A, the second portion Tb of the defect T is maintained in the state of being gripped by the second outer arm 32 and the central arm 2C.

In the treatment portion 10 of the clip device 100 according to the present example, the material and the configuration of the elastic member 29 may be appropriately determined to suitably grip the defect T of the biological tissue as the treatment target.

*First Modified Example*

Figure 25:
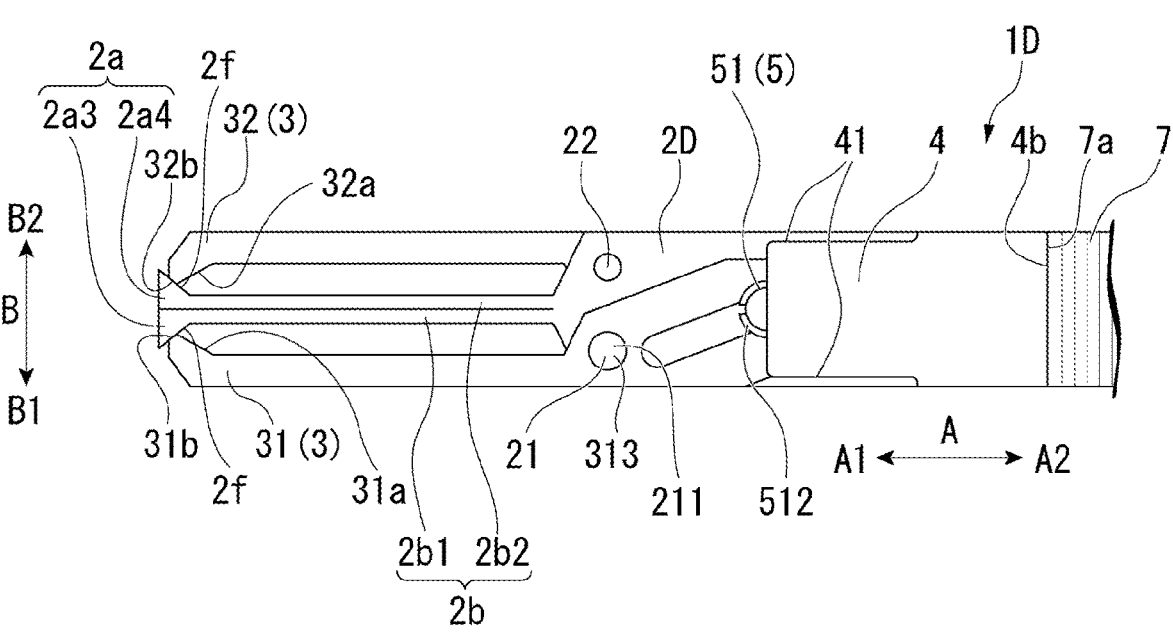
FIG. 25 is a side view showing an example of a configuration of a treatment portion of a clip according to a first modified example of the present disclosure.
Figure 26:
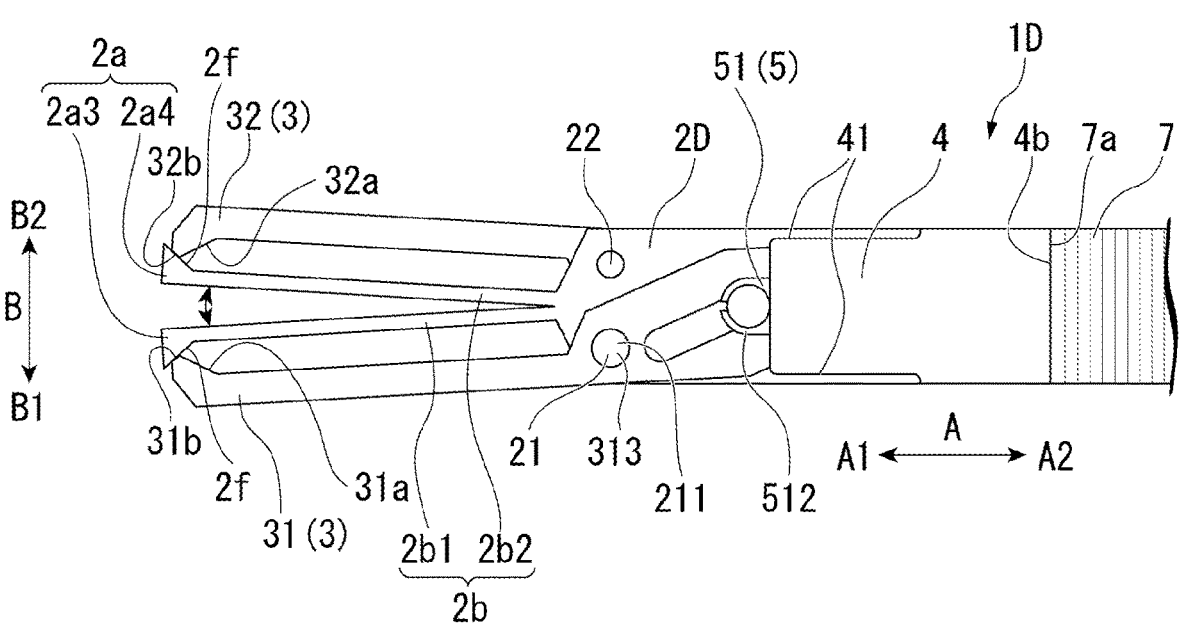
FIG. 26 is a side view showing an example of the configuration of the treatment portion of the clip according to the present modified example.
Figure 27:
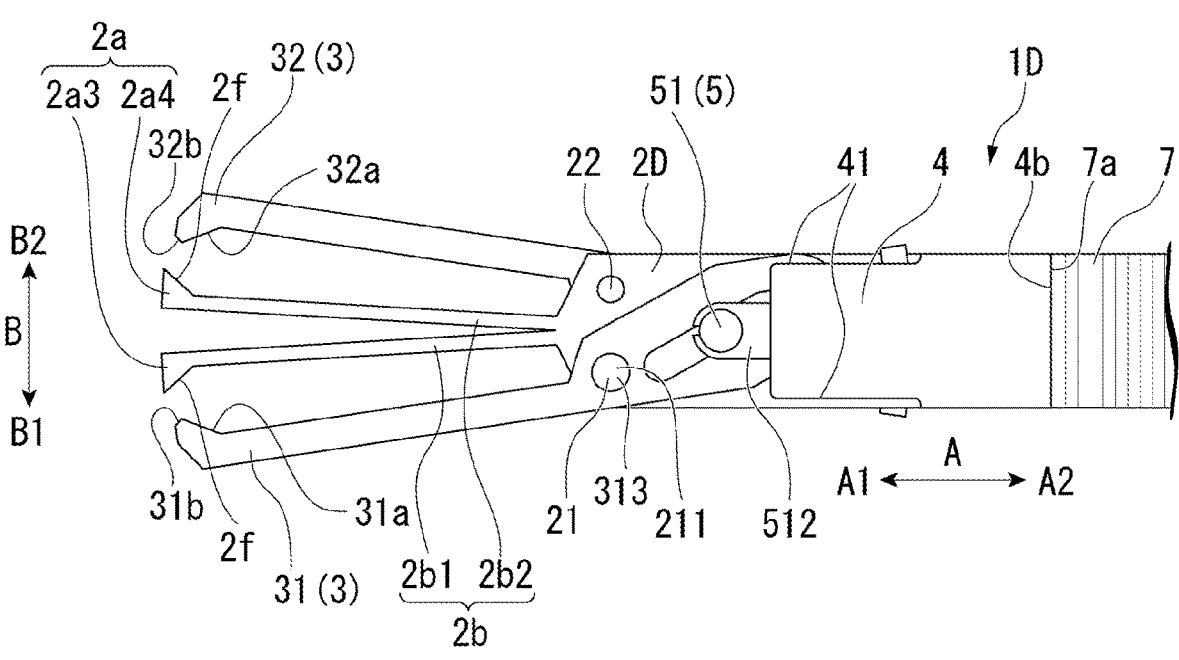
FIG. 27 is a side view showing an example of the configuration of the treatment portion of the clip according to the present modified example.
Figure 28:
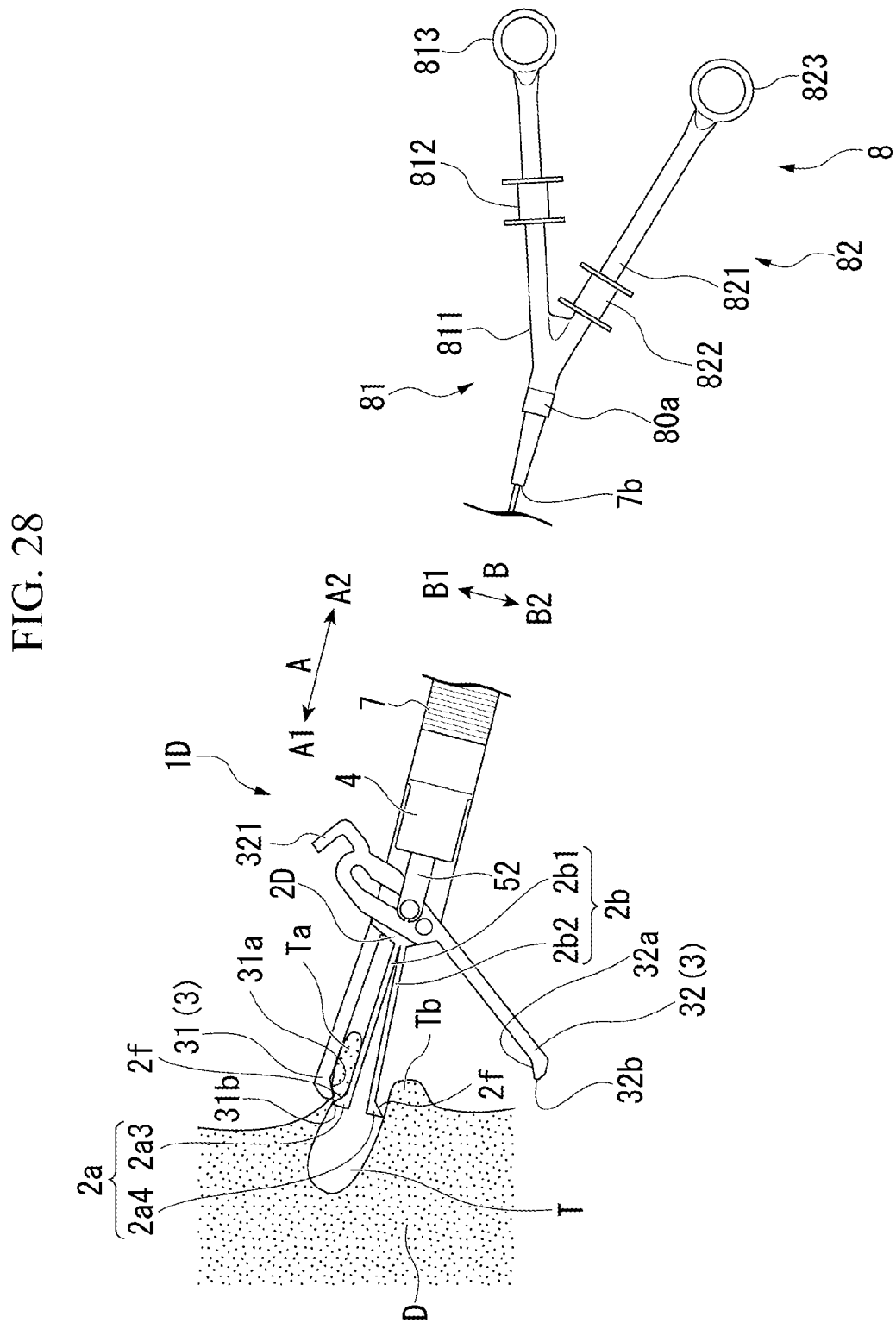
FIG. 28 is a schematic view showing an example of an operation of the treatment to the tissues using the clip.

Hereinafter, referring to FIG. 25 through FIG. 28, a treatment portion 1D of the clip device 100 according to the first modified example of the present example will be described. FIG. 25 through FIG. 27 are views showing the operations of the treatment portion 1D of the clip device 100 according to the present modified example. FIG. 28 is a view showing a ligation treatment with respect to the defect T of the biological tissue as the treatment target using the treatment portion 1D of the clip device 100 according to the present modified example.

As shown in FIG. 25 through FIG. 27, a configuration of the central arm 2D of the treatment portion 1D of the clip device 100 according to the present modified example is different from the central arm 2 according to the first example described above. More specifically, in the central arm 2D of the clip device 100 according to the present modified example, the rod-shaped portion 2*b* is configured to branch to the first rod-shaped portion 2*b*1 and the second rod-shaped portion 2*b*2 along the longitudinal direction A. In the rod-shaped portion 2*b*, an elastic member is provided between the first rod-shaped portion 2*b*1 and the second rod-shaped portion 2*b*2. Due to the elastic member provided between the first rod-shaped portion 2*b*1 and the second rod-shaped portion 2*b*2, the first rod-shaped portion 2*b*1 and the second rod-shaped portion 2*b*2 are biased to be separated from each other in the open-close direction B. Furthermore, as shown in FIG. 25, the central arm 2D includes a first distal end portion 2*a*3 and a second distal end portion 2*a*4 corresponding to the first rod-shaped portion 2*b*1 and the second rod-shaped portion 2*b*2. When the first outer arm 31 and the second outer arm 32 and the central arm 2D are in the closed state, the first distal end portion 2*a*3 and the second distal end portion 2*a*4 may be disposed at the distal end side A1 in the longitudinal direction A than the distal ends of the first outer arm 31 and the second outer arm 32. However, the configuration according to the present modified example is not limited thereto. For example, when the first outer arm 31 and the second outer arm 32 and the central arm 2D are in the closed state, the first distal end portion 2*a*3 and the second distal end portion 2*a*4 may be disposed at the proximal end side A2 in the longitudinal direction A than the distal ends of the first outer arm 31 and the second outer arm

32. The first distal end portion 2*a*3 and the second distal end portion 2*a*4 may be formed to have inclination surfaces 2*f* formed to be inclined from the respective distal end surface to the proximal end side, respectively. In the first outer arm 31, an engaging surface 31*b* connecting the distal end surface thereof and the inner surface 31*a* and being substantially parallel to the corresponding inclination surface 2*f* is formed. Similarly, in the second outer arm 32, an engaging surface 32*b* connecting the distal end surface thereof and the inner surface 32*a* and being substantially parallel to the corresponding inclination surface 2*f* is formed.

As shown in FIG. 26, the treatment portion 1D of the clip device 100 according to the present modified example has the above-described configuration such that when the operator retracts the first pulling member 51 or the second pulling member 52 to the proximal end side A2 in the longitudinal direction A, the first rod-shaped portion 2*b*1 and the second rod-shaped portion 2*b*2 are opened to be separated from each other in the open-close direction B by the biasing force of the elastic member. In the process, the inclination surface 2*f* of the first distal end portion 2*a*3 located on the distal end side A1 of the first rod-shaped portion 2*b*1 is engaged with the engaging surface 31*b* of the first outer arm 31, and the inclination surface 2*f* of the first distal end portion 2*a*4 located on the distal end side A1 of the second rod-shaped portion 2*b*2 is engaged with the engaging surface 32*b* of the second outer arm 32.

When the operator continues retracting the first pulling member 51 or the second pulling member 52 to the proximal side A2 in the longitudinal direction A, as shown in FIG. 27, the distance between the first distal end portion 2*a*3 and the second distal end portion 2*a*4 is further increased. In the treatment portion 1D of the clip device 100 according to the present modified example, the first distal end 2*a*3 and the second distal end 2*a*4 are configured to be opened in advance with the distance therebetween at a predetermined amount. Accordingly, when the first outer arm 31 is opened by the operation of the operator, a gap for disposing the biological tissue as the treatment target is formed between the first outer arm 31 and the first distal end portion 2*a*3 of the central arm 2D. Similarly, when the second outer arm 32 is opened by the operation of the operator, a gap for disposing the biological tissue as the treatment target is formed between the second outer arm 32 and the second distal end portion 2*a*4 of the central arm 2D.

FIG. 28 is a view showing a ligation treatment with respect to the biological tissue T as the treatment target using the treatment portion 1D of the clip device 100 according to the present modification. As shown in FIG. 28, the first portion Ta of the defect T of the biological tissue as the treatment target is gripped by the first outer arm 31 and the first rod-shaped part 2*b*1 of the central arm 2D. More specifically, the first portion Ta of the defect T is gripped between the engaging surface 31*b* of the first outer arm 31 and the inclination surface 2*f* of the first rod-shaped portion 2*b*1 of the central arm 2D. According to the treatment portion 1D according to the present example, since the first rod-shaped portion 2*b*1 of the central arm 2D is biased to the first side B1 of the open-close direction B, even if the operator unintentionally advances the first slider 812 of the operation portion 8 toward the distal end side A1 in the longitudinal direction A, the state in which the first portion Ta of the defect T is gripped by the first outer arm 31 and the first rod-shaped portion 2*b*1 of the central arm 2D may be maintained.

Similar to the traction step according to the first example described above, in the state of gripping the first portion Ta of the defect T, the operator pulls the entire treatment portion 1D to the vicinity of the second portion Tb of the defect T. Thereafter, the operator advances the second slider 822 of the operation portion 8 to the distal end side A1 in the longitudinal direction A such as to locate the second portion Tb of the defect T between the second rod-shaped portion 2b2 of the second outer arm 32 and the central arm 2D. As shown in FIG. 28, the second distal end portion 2a2 corresponding to the second rod-shaped portion 2b2 has an inclination surface 2f formed to be inclined to the proximal end side from the distal end surface thereof, and the second rod-shaped portion 2b2 is biased to open in the second side B2 of the open-close direction B such that it is easy to place the second rod-shaped portion 2b2 under the second portion Tb of the defect T.

In this state, when the operator retracts the second slider 822 of the operation portion 8 to the proximal end side A2 in the longitudinal direction A, the second outer arm 32 is rotated to the first side B1 in the open-close direction B toward the second rod-shaped portion 2b2 such that it is possible to grip the second portion Tb of the defect T by the second outer arm 32 and the second rod-shaped portion 2b2.

Similar to the above-described examples, according to the treatment portion 1D of the clip device 100 according to the present modified example, even if the operator does not operate the operation portion 8 of the clip device 100, the state in which the treatment target is gripped with an appropriate gripping force may be maintained. Furthermore, the treatment target is gripped by the engaging surface 31b of the first outer arm 31 and the inclination surface 2f of the first rod-shaped portion 2b1 of the central arm 2D, or by the engaging surface 32b of the second outer arm 32 and the inclination surface 2f of the second rod-shaped portion 2b2 of the central arm 2D, it is possible to prevent the treatment target from being damaged by the sharp portion.

Second Modified Example

Figure 29:
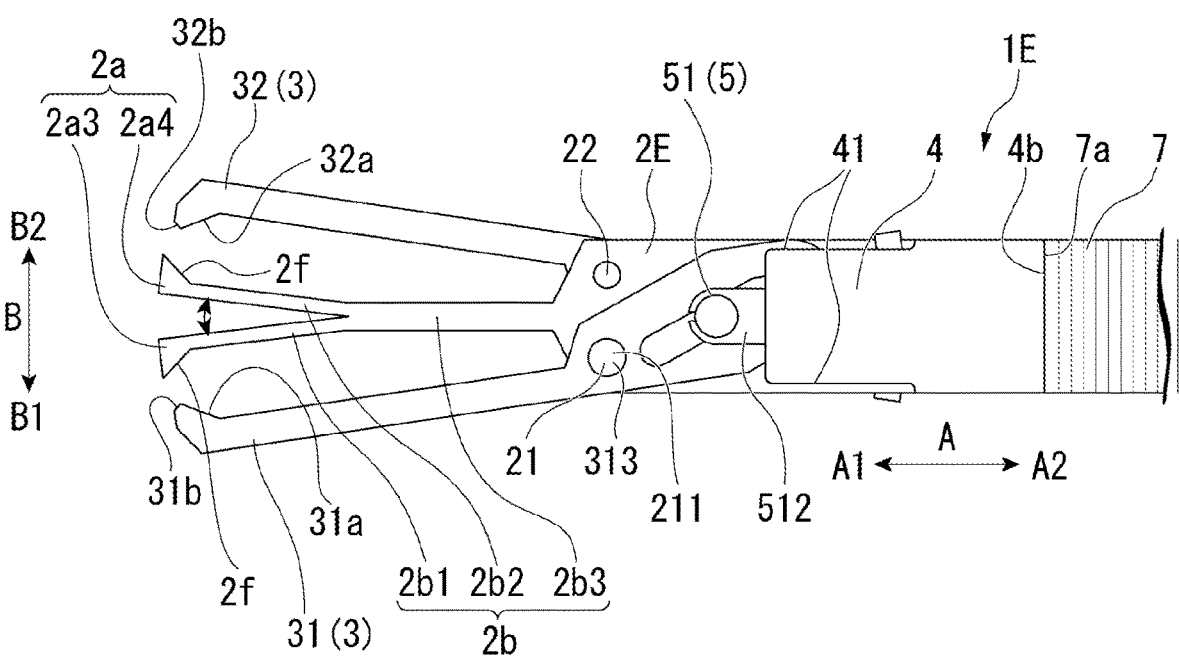
FIG. 29 is a side view showing an example of a configuration of a treatment portion of a clip according to a second modified example of the present disclosure.

Hereinafter, referring to FIG. 29, a configuration of a treatment portion 1E of the clip device 100 according to the present example will be described. The central arm 2D of the clip device 100 according to the first modified example described above is branched from a root portion thereof into the first rod-shaped portion 2b1 and the second rod-shaped portion 2b2. On the other hand, as shown in FIG. 29, the central arm 2E of the treatment portion 1E of the clip device 100 according to the present modified example is branched from a position close to a distal end thereof into the first rod-shaped portion 2b1 and the second rod-shaped portion 2b2. That is, the central arm 2E of the clip device 100 according to the present modified example is formed with a first rod-shaped portion 2b1, a second rod-shaped portion 2b2, and the proximal end rod-shaped portion 2b3. In the central arm 2E according to the present modified example, an elastic member (not shown) is provided between the first rod-shaped portion 2b1 and the second rod-shaped portion 2b2. Due to the elastic member provided between the first rod-shaped portion 2b1 and the second rod-shaped portion 2b2, the first rod-shaped portion 2b1 and the second rod-shaped portion 2b2 are biased to be separated from each other in the open-close direction B.

According to the treatment portion 1E of the clip device 100 according to the present modification, since the central arm 2E is branched at a position close to the distal end thereof, the biasing force by the elastic member provided between the first rod-shaped portion 2b1 and the second rod-shaped portion 2b2 is more reliably applied to the root portion of the defect T of the biological tissue as the treatment target. Generally, in the biological tissue such as the mucosa or the like, since the root portion is more rigid than the distal end portion, the root portion of the biological tissue may be gripped by a larger gripping force by the treatment portion 1E of the clip device 100 according to the present modified example, and it is possible to prevent the biological tissue from sliding down from the treatment portion 1E. According to the treatment portion 1E of the clip device 100 according to the present modified example, the ligation treatment may be performed with respect to the defects T of the biological tissue as the treatment target by the similar operations in the first modified example described above.

Third Example

Figure 30:
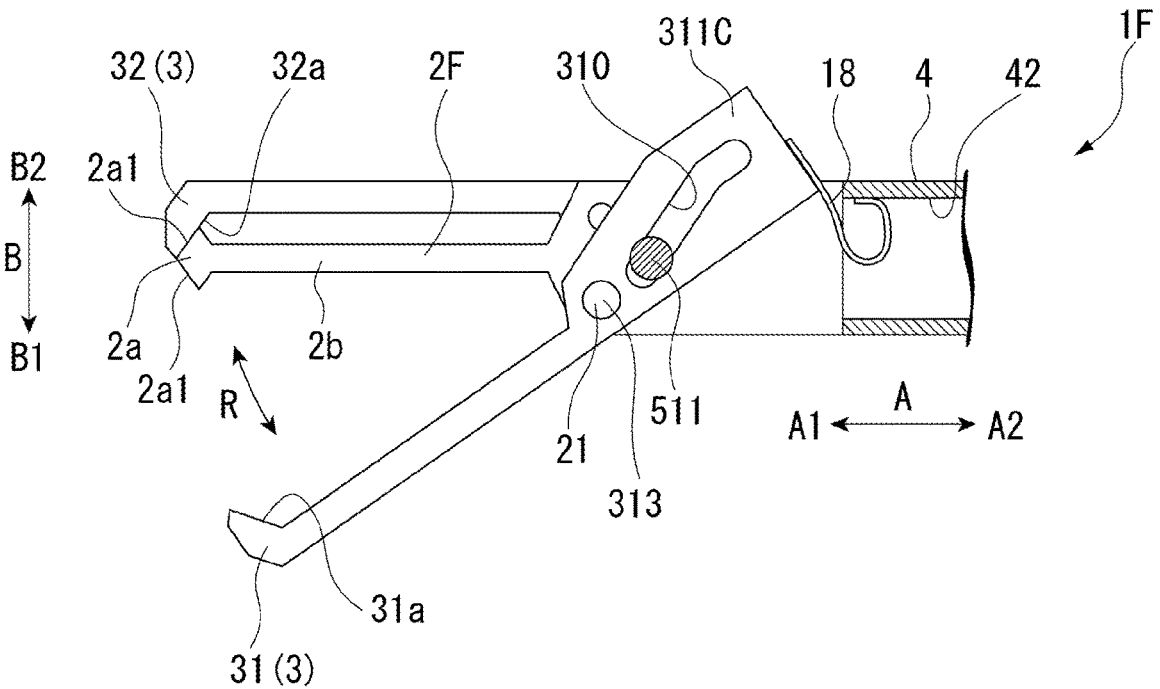
FIG. 30 is a side view showing an example of a configuration of a treatment portion of a clip according to a third example of the present disclosure.
Figure 31:
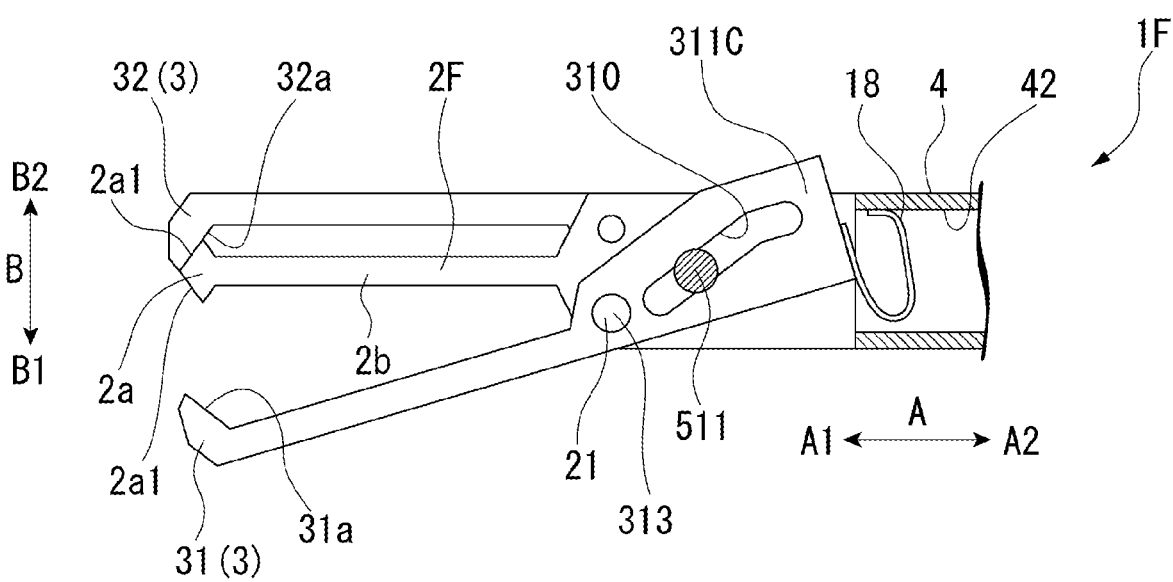
FIG. 31 is a side view showing an example of the configuration of the treatment portion of the clip according to the present disclosure.

Hereinafter, a configuration of a treatment portion 1F of the clip device 100 according to the third example of the present disclosure will be described with reference to FIG. 30 through FIG. 32. As shown in FIG. 30, in the treatment portion 1F of the clip device 100 according to the present example, an elastic member 18 is configured to connect a proximal end portion 311C of the first outer arm 31 and an inner peripheral surface 42 of the clip holder 4.

Similar to the above-described examples, the clip holder 4 according to the present example is a tubular structure having a longitudinal axis such as formed in a cylindrical shape. As shown in FIG. 30, the elastic member 18 for biasing the first outer arm 31 to rotate in the open-close direction B is provided between the proximal end surface of the proximal end portion 311C of the first outer arm 31 and the inner peripheral surface 42 of the clip holder 4. The elastic member 18 is disposed at a position in contact with the inner peripheral surface 42 of the clip holder 4, and it is not necessary to fix the elastic member 18 to the inner peripheral surface 42 of the clip holder 4. The elastic member 18 may be formed, for example, by using various leaf spring configurations. More specifically, as shown in FIG. 31, due to the biasing force of the elastic member 18 according to the present example, in a state in which there is no external force is applied, the first outer arm 31 is biased such that the distal end portion thereof is rotated toward the distal end portion 2a of the central arm 2F in the second side B2 of the open-close direction B. The material and the configuration of the elastic member 18 may be appropriately selected according to the characteristic of the biological tissue to be treated, the treatment location, or the like.

Figure 32:
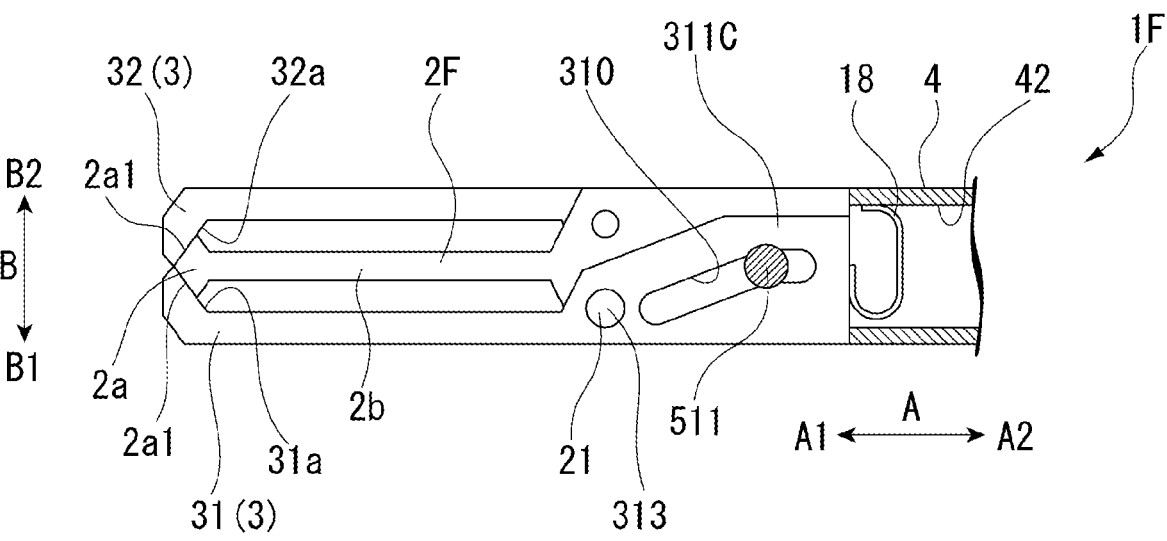
FIG. 32 is a side view showing an example of the configuration of the treatment portion of the clip according to the present disclosure.

Furthermore, as shown in FIG. 32, when the first outer arm 31 and the second outer arm 32 and the central arm 2F according to the present example are in the closed state, the distal ends of the first outer arm 31 and the second outer arm 32 are positioned on the distal end side A1 in the longitudinal direction A than the distal end of the central arm 2F. That is, as shown in FIG. 32, when the first outer arm 31 and the second outer arm 32 and the central arm 2F are in the closed state, the inner surface 31a of the first outer arm 31 and the inner surface 32a of the second outer arm 32 abut against the distal end surface 2a1 of the distal end portion 2a of the central arm 2F.

According to the treatment portion 1F of the clip device 100 according to the present example, due to the elastic member 18 provided between the proximal end surface of the proximal end portion 311C of the first outer arm 31 and the inner peripheral surface 42 of the clip holder 4, the treatment target positioned between the first outer arm 31 and the central arm 2F may be gripped with the appropriate gripping force. According to the treatment portion 1F of the clip device 100 according to the present example, similar to the above-described examples, even if the operator does not continue gripping the first slider 812 of the operation portion 8, the defect T of the biological tissue as the treatment target may be maintained in a state of being gripped by the first outer arm 31 and the central arm 2F.

In the present example, the configuration in which the elastic member 18 is provided between the proximal end surface of the proximal end portion 311C of the first outer arm 31 and the inner peripheral surface 42 of the clip holder 4 is described; however, the present example is not limited thereto. The elastic member 18 is configured to connect the first arm 31 and the clip holder 4, and the configuration may be appropriately modified.

In the present example, the elastic member 18 may be provided in either of the first outer arm 31 or the second outer arm 32. More specifically, when a ligation treatment is performed with respect to the defect T of the biological tissue as the treatment target in the present disclosure, the elastic member 18 may be provided only on the outer arm 3 configured to grip the first portion Ta of the defect T at first. However, according to the configuration in which the elastic member 18 is provided on both the first outer arm 31 and the second outer arm 32, it is unnecessary for the operator to be aware of recognizing the first outer arm 31 and the second outer arm 32 to be used such that is it possible to simplify the treatment.

Modifications Example

Figure 33:
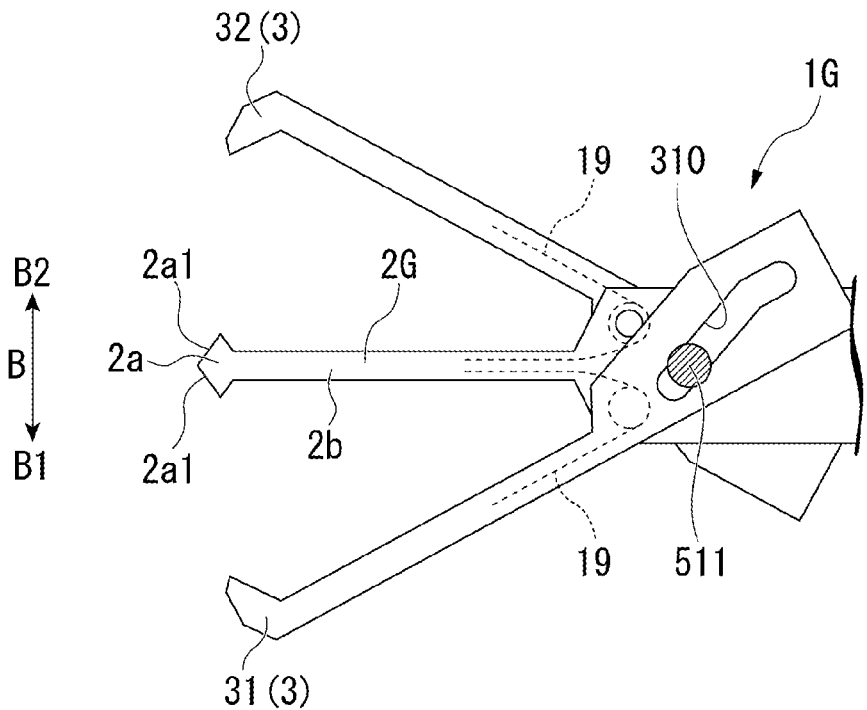
FIG. 33 is a side view showing an example of a configuration of a treatment portion of a clip according to a modified example of the present disclosure.

Hereinafter, referring to FIG. 33, a configuration of a treatment portion 1G of the clip device 100 according to the modified example of the present example will be described. As shown in FIG. 33, in the treatment portion 1G of the clip device 100 according to the present modification, an elastic member 19 is provided to connect the first outer arm 31 and the central arm 2G. Similarly, the elastic member 19 is provided between the second outer arm 32 and the central arm 2G for connecting the second outer arm 32 and the central arm 2G. More specifically, for example, according to the elastic member 19 provided between the proximal end portion of the first outer arm 31 and the central arm 2G, in a state in which the external force is not applied, the first outer arm 31 is biased such as to be rotated toward the central arm 2G in the second side B2 of the open-close direction B. On the other hand, according to the elastic member 19 provided between the proximal end portion of the second outer arm 32 and the central arm 2G, in the state in which the external force is not applied, the second outer arm 32 is biased such as to be rotated toward the central arm 2G in the first side B1 of the open-close direction B. The elastic member 19 according to the present modified example may be configured, for example, using various spring hinge configurations.

In the present embodiment, the elastic member 19 may be provided on only one of the first outer arm 31 and the second outer arm 32. More specifically, when a ligation treatment is performed with respect to the defect T of the biological tissue as the treatment target in the present disclosure, the elastic member 19 may be provided only on the outer arm 3 configured to grip the first portion Ta of the defect T at first. However, according to the configuration in which the elastic member 19 is provided on both the first outer arm 31 and the second outer arm 32, it is unnecessary for the operator to be aware of recognizing the first outer arm 31 and the second outer arm 32 to be used such that is it possible to simplify the treatment.

1. A three-arm clip, comprising: a central arm; a pair of outer arms configured to rotatably connect to the central arm; a slide pin configured to advance and retract along a longitudinal direction of the central arm; a grasping force adjustment mechanism provided in either of the central arm and the pair of outer arms and configured to adjust a grasping force by the central arm and the pair of outer arms; a releasing mechanism detachably connected to the slide pin; and a force transmitter mechanism configured to advance and retract the slide pin that is connected to the release mechanism, wherein the pair of outer arms includes an outer arm slot in which the slide pin is slidable, and the pair of outer arms open and close when the slide pin advances and retracts along the longitudinal direction to slide in the outer arm slot.

2. The three-arm clip according to the example 1, wherein the grasping force adjustment mechanism includes a plurality of teeth formed in the outer arm slot, and
   the plurality of teeth are configured to restrict the slide pin from sliding along the outer arm slot.

3. The three-arm clip according to the example 1,
   wherein the central arm includes a central arm slot, the slide pin is provided to be slidable in the central arm slot, and a longitudinal direction of the central arm slot is the same with the advance-retract direction of the slide pin.

4. The three-arm clip according to the example 3, wherein the grasping force adjustment mechanism includes a plurality of teeth formed in the central arm slot, and the plurality of teeth are configured to restrict the slide pin from sliding along the central arm slot.

5. The three-arm clip according to the example 1, further comprising a clip holder configured to accommodate a proximal end portion of the pair of outer arms; wherein the grasping force adjustment mechanism comprises: a plurality of teeth formed at a proximal end of the pair of outer arms; and a matching member provided at an inner side of the clip holder, the matching member configured to engage with the plurality of teeth.

6. The three-arm clip according to the example 5, wherein the matching member is a pawl or a gear rack.

7. The three-arm clip according to the example 1, further comprising a sheath, wherein the grasping force adjustment mechanism is a spring provided between the central arm slot provided in the central arm and the sheath, and a proximal end portion of the central arm has an elasticity so as to press the central arm toward a distal end side due to a restoration force of the spring.

8. The three-arm clip according to the example 7, wherein the central arm includes two branch arms bifurcated and disposed at a proximal end portion of the central arm and, and the two branch arms are biased so as to move outwardly in a radial direction to be separated from each other as toward each distal end of the two branch arms due to the restoration force of the spring.

9. The three-arm clip according to the example 7, wherein the central arm includes two branch arms bifurcated and disposed at a distal end portion of the central arm, and the two branch arms are biased so as to move outwardly in a radial direction to be separated from each other as toward each distal end of the two branch arms due to the restoration force of the spring.

10. The three-arm clip according to the example 1, further comprising pressing tube at a proximal end of the pair of outer arms, wherein the grasping force adjustment mechanism is a leaf spring disposed between a proximal end of the pair of outer arms and the pressing tube, and distal ends of the pair of outer arms are biased in a closing direction inwardly along the radial direction due to a restoration force of the leaf spring.

11. The three-arm clip according to the example 1, wherein the grasping force adjustment mechanism is a spring disposed between the pair of outer arms, and distal ends of the pair of outer arms are biased in a closing direction inwardly along the radial direction due to a restoration force of the spring.

12. The three-arm clip of any according to any one from the example 1 to the example 11, wherein the force transmitter mechanism comprises an operation wire configured to control a movement of the pair of outer arms.

13. A clip, comprising: a central arm including a first pin, a first slot, and a second pin being movable in the first slot; a pair of outer arms including a second slot in which the second pin is slidable, the pair of outer arms being rotatably connected to the central arm by the first pin; a wire detachably connected to the central arm or the pair of outer arms and configured to drive open-close operation of the pair of outer arms; and a grasping force adjustment mechanism including an end provided in the central arm or the pair of outer arms and configured to adjust a grasping force for grasping tissues.

14. The clip according to the example 13, wherein the grasping force adjustment mechanism comprises a ratchet provided within the first slot or the second slot, the ratchet comprising a plurality of teeth.

15. The clip according to the example 13, wherein the pair of outer arms are configured to extend toward the distal end side of the central arm, the grasping force adjustment mechanism includes a biasing member provided in the central arm, and the biasing member is configured to bias the central arm toward the distal end side.

16. The clip according to the example 13, wherein the pair of outer arms include a first outer arm and a second outer arm configured to sandwich the central arm, the central arm includes a first central arm being biased in a direction approaching the first outer arm and a second central arm being biased in a direction approaching the second outer arm, and the first central arm and the second central arm function as the grasping force adjustment mechanism.

17. A tissue closure method, comprising: grasping a first portion of tissue by a first arm and a central arm; adjusting a grasping force for grasping the first portion to maintain a state in which the first portion is grasped; moving the first portion in a direction approaching a second portion of the tissue in the state in which the first portion is grasped by adjusting the grasping force; and grasping the second portion by the central arm and a second arm after the first portion is moved in the vicinity of the second portion.

18. The tissue closure method according to the example 17, comprising: fixing relative positions of the first arm and the central arm by a ratchet provided in the first arm or the central arm; and maintaining the grasping force for grasping the first portion by fixing the relative positions of the first arm and the central arm.

19. The tissue closure method according to the example 17, comprising: moving the first arm and the central arm to make the first portion to be disposed between the first arm and the central arm in a longitudinal direction of the first arm; pressing the central arm toward the first arm by a biasing member provided in the central arm; and maintaining the grasping force for grasping the first portion by pressing the central arm toward the first arm.

20. The tissue closure method according to the example 17, wherein the central arm includes a first central arm biased in a direction approaching the first arm and a second central arm biased in a direction approaching the second arm, the tissue closure method comprising: maintaining the grasping force for grasping the first portion by grasping the first portion by the first arm and the central arm.

What is claimed is:

1. A clip comprising:
a central arm defining an elongate first slot;
a pair of outer arms including a first outer arm, the first outer arm defining an elongate second slot;
a first pin rotatably engaging the central arm and the first outer arm;
a second pin configured to move translationally along the first slot and the second slot;
a force transmitter detachably attached to the central arm or the pair of the outer arms, the force transmitter is configured to actuate the pair of the outer arms to open or close the outer arms; and
a ratchet located within the first slot or the second slot,
wherein the first slot or the second slot comprise a first region that restricts translational movement of the second pin by the ratchet, and a second region that allows unrestricted translational movement of the second pin.

2. The clip of claim 1, wherein the ratchet comprises a plurality of teeth and the plurality of teeth is disposed in the first region.

3. The clip of claim 2, wherein the first region has a length that is less than or equal to half a length of the first slot or the second slot.

4. The clip of claim 2, wherein the first region is provided on a proximal side of the first slot or the second slot.

5. The clip of claim 4, wherein the second region is provided on a distal side of the first slot or the second slot.

6. The clip of claim 5, wherein the second region comprises a flat surface configured to allow the second pin to slide.

7. The clip of claim 1, comprising:
a clip holder located at a proximal end of the pair of the outer arms, and wherein the ratchet is configured to be within a width of the clip holder when the outer arms close.

8. The clip of claim 1, wherein a force required for the second pin to overcome the ratchet is smaller than a force required to disengage the force transmitter from the central arm or the pair of outer arms.

9. The clip of claim 1, wherein the ratchet is configured to adjustably maintain a force for gripping tissue between the central arm and the first outer arm.

10. A clip comprising:
a central arm defining an elongate first slot;
a pair of outer arms including a first outer arm, the first outer arm defining an elongate second slot;
a first pin rotatably engaging the central arm and the first outer arm;
a second pin attached to the first outer arm and configured to move translationally along the first slot and the second slot;
a force transmitter detachably attached to the central arm or the pair of the outer arms, the force transmitter is configured to actuate the pair of the outer arms to open or close the outer arms; and a retention feature configured to adjustably maintain a force for gripping tissue between the central arm and the first outer arm, wherein the retention feature comprises a ratchet located within the first slot or the second slot, the ratchet comprising a plurality of teeth, and wherein the first slot or the second slot comprise a first region that restricts translational movement of the second pin by the ratchet, and a second region that allows unrestricted translational movement of the second pin.

11. The clip of claim 10, wherein the plurality of teeth is disposed in the first region.

12. The clip of claim 10, wherein the first region is provided on a proximal side of the first slot or the second slot.

13. The clip of claim 12, wherein the second region is provided on a distal side of the first slot or the second slot.

14. The clip of claim 13, wherein the second region comprises a flat surface configured to allow the second pin to slide.

15. A multi-arm clip comprising:

a central arm;

a first outer arm configured to rotatably connect to the central arm;

a slide pin configured to move translationally along a longitudinal axis direction of the central arm to open or close the first outer arm using an outer arm slot defined by the first outer arm;

a retention feature provided on the first outer arm, the retention feature configured to maintain a gripping force between the central arm and the first outer arm in an adjustable manner; and a force transmitter configured to move the slide pin translationally along the longitudinal axis direction;

wherein the outer arm slot is an elongate slot that is configured to make the slide pin movable translationally, and wherein the retention feature includes a plurality of teeth configured to restrict the slide pin from sliding along the outer arm slot, and wherein the outer arm slot comprises a first region that restricts translational movement of the slide pin by the teeth, and a second region that allows unrestricted translational movement of the slide pin.

16. The multi-arm clip of claim 15, wherein the central arm defines a central arm slot; and wherein the slide pin is configured to slide along the central arm slot in the longitudinal axis direction of the central arm.

17. The clip of claim 15, wherein the first region is provided on a proximal side of the outer arm slot.

18. The clip of claim 17, wherein the second region is provided on a distal side of the outer arm slot.

19. The clip of claim 18, wherein the second region comprises a flat surface configured to allow the slide pin to slide.

* * * * *